(12) United States Patent
McCormack et al.

(10) Patent No.: US 7,972,813 B2
(45) Date of Patent: Jul. 5, 2011

(54) TETRODOTOXIN-RESISTANT SODIUM CHANNEL ALPHA SUBUNIT

(75) Inventors: Kenneth McCormack, Raleigh, NC (US); Christopher Raj Dinesh, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 48 days.

(21) Appl. No.: 11/540,143

(22) Filed: Sep. 29, 2006

(65) Prior Publication Data

US 2007/0111943 A1 May 17, 2007

Related U.S. Application Data

(60) Provisional application No. 60/722,563, filed on Sep. 30, 2005.

(51) Int. Cl.
C07H 21/04 (2006.01)
C12Q 1/68 (2006.01)
C12P 21/04 (2006.01)
C12N 1/20 (2006.01)

(52) U.S. Cl. ....... 435/70.1; 435/6; 435/69.1; 435/252.3; 530/350; 536/23.5; 536/24.31

(58) Field of Classification Search ............. 435/6, 69.1, 435/91.1, 91.31, 70.1, 252.3; 536/23.1, 23.5, 536/24.5, 24.31; 530/350
See application file for complete search history.

(56) References Cited

U.S. PATENT DOCUMENTS

| | | | |
|---|---|---|---|
| 4,554,101 A | 11/1985 | Hopp | |
| 4,861,719 A | 8/1989 | Miller | |
| 5,093,246 A | 3/1992 | Cech et al. | |
| 5,139,941 A | 8/1992 | Muzyczka et al. | |
| 5,252,479 A | 10/1993 | Srivastava | |
| 5,328,688 A | 7/1994 | Roizman | |
| 5,380,836 A | 1/1995 | Rogart | |
| 5,437,982 A | 8/1995 | Catterall et al. | |
| 5,474,935 A | 12/1995 | Chatterjee et al. | |
| 5,585,362 A | 12/1996 | Wilson et al. | |
| 5,599,673 A * | 2/1997 | Keating et al. ................... | 435/6 |
| 5,622,856 A | 4/1997 | Natsoulis | |
| 5,658,776 A | 8/1997 | Flotte et al. | |
| 5,661,033 A | 8/1997 | Ho et al. | |
| 5,670,488 A | 9/1997 | Gregory et al. | |
| 5,686,278 A | 11/1997 | Williams et al. | |
| 5,693,509 A | 12/1997 | Cotten et al. | |
| 5,693,756 A | 12/1997 | Li et al. | |
| 5,707,618 A | 1/1998 | Armentano et al. | |
| 5,770,414 A | 6/1998 | Gage et al. | |
| 5,773,289 A | 6/1998 | Samulski et al. | |
| 5,776,859 A | 7/1998 | Nickel | |
| 5,789,390 A | 8/1998 | Descamps et al. | |
| 5,824,544 A | 10/1998 | Armentano et al. | |
| 5,830,725 A | 11/1998 | Nolan et al. | |
| 5,830,727 A | 11/1998 | Wang et al. | |
| 5,834,441 A | 11/1998 | Philip et al. | |
| 5,849,571 A | 12/1998 | Glorioso et al. | |
| 5,851,521 A | 12/1998 | Branellec et al. | |
| 5,856,152 A | 1/1999 | Wilson et al. | |
| 5,863,541 A | 1/1999 | Samulski et al. | |
| 5,879,934 A | 3/1999 | DeLuca | |
| 5,888,502 A | 3/1999 | Guber et al. | |
| 5,892,018 A | 4/1999 | Welsh et al. | |
| 6,030,810 A | 2/2000 | Delgado et al. | |
| 6,060,271 A | 5/2000 | Walewski et al. | |
| 6,184,349 B1 * | 2/2001 | Herman et al. ................ | 530/350 |
| 6,335,172 B1 | 1/2002 | Delgado et al. | |
| 6,479,259 B1 | 11/2002 | Herman et al. | |
| 6,479,498 B1 | 11/2002 | Marquess et al. | |
| 6,559,154 B2 | 5/2003 | Kang et al. | |
| 6,607,741 B2 | 8/2003 | Boucher, Jr. | |
| 6,613,345 B2 | 9/2003 | Boucher, Jr. | |
| 6,646,012 B2 | 11/2003 | Choi et al. | |
| 6,686,193 B2 | 2/2004 | Maher et al. | |
| 6,756,400 B2 | 6/2004 | Chinn et al. | |

FOREIGN PATENT DOCUMENTS

| | | |
|---|---|---|
| WO | WO 84/03564 | 9/1984 |
| WO | WO 91/09955 | 7/1991 |
| WO | WO 92/20808 | 11/1992 |
| WO | WO 93/23569 | 11/1993 |
| WO | WO 96/02651 | 2/1996 |
| WO | WO 03/016917 * | 2/2003 |

OTHER PUBLICATIONS

Baichwal et al., "Vectors for gene transfer derived from animal DNA viruses: Transient and stable expression of transferred genes," Gene Transfer, Kucherlapati R, Ed., Plenum Press, New York,117-148 (1986).
Balazy, "Clinical management of chronic pain in spinal cord injury," Clin J Pain, 8:102-110 (1992).
Barany and Merrifield, "Solid-phase peptide synthesis," In: The Peptides, Gross and Meienhofer, Eds., Academic Press, New York, 1-284 (1979).
Bitter et al., "Expression and secretion vectors for yeast," Methods in Enzymol, 153: 516-544 (1987).
Black et al, "Sodium channel mRNAs I, II and III in the CNS: cell-specific expression," Mol Brain Res, 22:275-289 (1994).
Cane et al., "Harnessing the Biosynthetic Code: Combinations, Permutations, and Mutations," Science, 282:63-68 (1998).
Coward et al., "Immunolocalization of SNS/PN3 and NaN/SNS2 sodium channels in human pain states," Pain, 85:41-50 (2000).
Devor, et al., "Na+ channel immunolocalization in peripheral mammalian axons and changes following nerve injury and neuroma formation," J Neurosci, 13:1976-1992 (1993).
Dixon, "Efficient analysis of experimental observations," Ann. Rev. Pharmacol. Toxicol., 20:441-462 (1980).
Drew et al., "Responses of spinal neurones to cutaneous and dorsal root stimuli in rats with mechanical allodynia after contusive spinal cord injury," Brain Res, 893:59-69 (2001).
Elbashir et al., "Duplexes of 21-nucleotide RNAs mediate RNA interference in cultured mammalian cells," Nature, 411:494-498 (2001).

(Continued)

Primary Examiner — Jane Zara
(74) Attorney, Agent, or Firm — Ropes & Gray LLP; James F. Haley, Jr.; Karen Mangasarian

(57) ABSTRACT

The present invention is directed to a chimp sodium channel alpha subunit and methods and compositions for making and using the same.

12 Claims, No Drawings

OTHER PUBLICATIONS

Fairbanks et al., "Agmatine reverses pain induced by inflammation, neuropathy, and spinal cord injury," *Proc Natl Acad Sci*, 97:10584-10589 (2000).

Fire et al.,"Potent and specific genetic interference by double-stranded RNA in *Caenorhabditis elegans*," *Nature*, 391: 806-811 (1998).

Gallo et al., "Modulation of non-N-methyl-D-aspartate receptors in cultured cerebellar granule cells," *J. Neurochem*, 54:1619-1625 (1990).

Hains et al., "Serotonergic neural precursor cell grafts attenuate bilateral hyperexcitability of dorsal horn neurons after spinal hemisection in rat," *Neuroscience*, 116:1097-1110 (2001).

Hains et al., "Temporal plasticity of dorsal horn somatosensory neurons after acute and chronic spinal cord hemisection in rat," *Brain Res*, 970:238-241 (2003).

Hannon, "RNA interference," *Nature*, 418:244-251 (2002).

Hao et al., "Allodynia-like effects in rat after ischaemic spinal cord injury photochemically induced by laser irradiation," *Pain*, 45:175-185 (1991).

Hefti, "Neurotrophic factor therapy for nervous system degenerative diseases", *J. Neurobiology*, 25:1418-1435 (1994).

Houston et al., "The chemical-biological interface: developments in automated and miniaturised screening technology," *Curr. Opin. Biotechnol.*, 8: 734-740 (1997).

Hulsebosch et al., "Rodent model of chronic central pain after spinal cord contusion injury and effects of gabapentin," *J Neurotrauma*, 17:1205-1217 (2000).

Ikeda-Yamasaki et al., "Projection map of the reaction center-light harvesting 1 complex from *Rhodopseudomonas viridis* at 10 Å resolution," *FEBS Lett.*, 425:505-508 (1998).

Jap et al., "2D crystallization: from art to science," *Ultramicros*, 46:45-84 (1992).

Jayawickreme et al., "Gene expression systems in the development of high-throughput screens," *Curr. Opin. Biotechnol.*, 8: 629-634 (1997).

Johnson et al., "Peptide Turn Mimetics," Chapter 14:366-378, Biotechnology and Pharmacy, Pezzuto JM et al., Eds., Chapman and Hall, New York (1993).

Kim et al., "An experimental model for peripheral neuropathy produced by segmental spinal nerve ligation in the rat," *Pain*, 50:355-363 (1992).

Kühlbrandt, "Two-dimensional crystallization of membrane proteins," *Q. Rev. Biophys.*, 25:1-49 (1992).

Kyte et al., "A simple method for displaying the hydropathic character of a protein," *J. Mol. Biol.*, 157:105-132 (1982).

Lacapère et al., "Two-dimensional crystallization of Ca-ATPase by detergent removal," *Biophys. J.*, 75:1319-1329 (1998).

Lai et al., "Inhibition of neuropathic pain by decreased expression of the tetrodotoxin-resistant sodium channel, NaV1.8," *Pain*, 95:143-152 (2002).

Lindsey et al., "An analysis of changes in sensory thresholds to mild tactile and cold stimuli after experimental spinal cord injury in the rat," *Neurorehabil Neural Repair*, 14:287-300 (2000).

Macejak et al., "Internal initiation of translation mediated by the 5' leader of a cellular mRNA," *Nature*, 353:90-94 (1991).

Mansikka et al., "Nerve injury-induced mechanical but not thermal hyperalgesia is attenuated in neurokinin-1 receptor knockout mice," *Exp Neurol*, 162:343-349 (2000).

Matzner et al., "Hyperexcitability at sites of nerve injury depends on voltage-sensitive Na+ channels," *J Neurophysiol*, 72:349-359 (1994).

McManus et al., "Gene silencing in mammals by small interfering RNAs," *Nat. Rev. Genet.*, 3:737-747 (2002).

Merrifield, "Solid phase synthesis," *Science*, 232:341-347 (1986).

Mills et al., "Strain and model differences in behavioral outcomes after spinal cord injury in rat ," *J. Neurotrauma*, 18:743-756 (2001).

Montoya et al., "Two-dimensional crystallization and preliminary structure analysis of light harvesting II (B800-850) complex from the purple bacterium *Rhodovulum sulfidophilum,*" *J. Mol. Biol.*, 250:1-10 (1995).

Mosser, "Two-dimensional crystallogenesis of transmembrane proteins," *Micron.*, 32:517-540 (2001).

Myers, "Will combinatorial chemistry deliver real medicines?" *Curr. Opin. Biotechnol.*, 8:701-707 (1997).

Ng et al., "SIFT: Predicting amino acid changes that affect protein function," *Nucleic Acid. Res.*, 31:3812-3814 (2003).

Nicolas et al., "Retroviral Vectors" in Vectors: A survey of molecular cloning vectors and their uses, Rodriguez R.L. & Denhardt D.T. (Eds.), Butterworth Publisher, Stoneham, 493-513 (1988).

Nogales et al., "Structure of the αβ tubulin dimer by electron crystallography," *Nature*, 391:199-203 (1998).

Novakovic et al "Distribution of the tetrodotoxin-resistant sodium channel PN3 in rat sensory neurons in normal and neuropathic conditions," *J Neurosci*, 18:2174-2187 (1998).

Ogata et al., "Molecular diversity of structure and function of the voltage-gated Na+ channels," *Jpn J Pharmacol*, 88:365-377 (2002).

Pelletier et al., "Internal initiation of translation of eukaryotic mRNA directed by a sequence derived from poliovirus RNA," *Nature*, 334:320-325 (1988).

Porreca et al., "A comparison of the potential role of the tetrodotoxin-insensitive sodium channels, PN3/SNS and NaN/SNS2, in rat models of chronic pain ," *Proc Natl Acad Sci*, 96:7640-7644 (1999).

Qu et al., "Differential modulation of sodium channel gating and persistent sodium currents by the beta1, beta2, and beta3 subunits," *Mol. Cell. Neurosci.*, 18:570-80 (2001).

Reich et al., "Small interfering RNA (siRNA) targeting VEGF effectively inhibits ocular neovascularization in a mouse model," *Mol. Vis.*, 9:210-216 (2003).

Ridgeway, "Mammalian expression vectors," in Vectors: A survey of molecular cloning vectors and their uses. Rodriguez RL, Denhardt DT, Eds. Butterworth Publishers, Stoneham, 467-492 (1988).

Rigaud et al., "Bio-Beads: an efficient strategy for two-dimensional crystallization of membrane proteins," *J. Struct. Bioi.*, 118:226-235 (1997).

Scharf et al, "Heat stress promoters and transcription factors," *Results Probl. Cell Differ.*, 20:125-62 (1994).

Scheuring et al., "High-resolution AFM topographs of Rubrivivax gelatinosus light-harvesting complex LH2," *EMBO J.*, 20:3029-3035 (2001).

Song et al., "RNA interference targeting Fas protects mice from fulminant hepatitis," *Nat. Med.*, 9:347-351 (2003).

Tam et al., "$S_N2$ deprotection of synthetic peptides with a low concentration of HF dimethyl sulfide: evidence and application in peptide synthesis," *J. Am. Chem. Soc.*, 105:6442-6455 (1983).

Tanaka et al., "SNS Na+ channel expression increases in dorsal root ganglion neurons in the carrageenan inflammatory pain model," *Neuroreport*, 9:967-972 (1998).

Tao et al., "Expression of PSD-95/SAP90 is critical for N-methyl-D-aspartate receptor-mediated thermal hyperalgesia in the spinal cord," *Neuroscience*, 98:201-206 (2000).

Temin, "Retrovirus vectors for gene transfer: Efficient integration into and expression of exogenous DNA in vertebrate cell genome," In Gene Transfer, Kucherlapati R, Ed., Plenum Press, New York, 149-187 (1986).

Turner et al., "Chronic pain associated with spinal cord injuries: a community survey," *Arch Phys Med Rehabil*, 82:501-508 (2001).

Walz et al, "Projection structures of three photosynthetic complexes from Rhodobacter sphaeroides: LH2 at 6 Å, LH1 and RC-LH1 at 25 Å," *J. Mol. Biol.*, 282:833-845 (1998).

Wood et al, "Voltage-gated sodium channels and pain pathways," *J Neurobiol.*, 61:55-71 (2004).

Yezierski et al., "The mechanosensitivity of spinal sensory neurons following intraspinal injections of quisqualic acid in the rat," *Neurosci Lett*, 157:115-119 (1993).

Zerangue et al, "A new ER trafficking signal regulates the subunit stoichiometry of plasma membrane $K_{ATP}$ channels," *Neuron*, 22:537-548 (1999).

\* cited by examiner

TETRODOTOXIN-RESISTANT SODIUM CHANNEL ALPHA SUBUNIT

CROSS-REFERENCE TO RELATED APPLICATIONS

This application claims the benefit under 35 U.S.C. §119 of U.S. Provisional application Ser. No. 60/722,563 filed Sep. 30, 2005, the entire contents of which is incorporated herein by reference.

BACKGROUND

1. Field of the Invention

The present invention is generally directed to voltage-gated sodium channel NaV1.8 from *Pan troglodytes* (chimp). The invention further describes methods and compositions for the stable expression of chimp NaV1.8 sodium channels and methods of use of such compositions for identifying compounds that modulate the activity of sodium channels.

2. Background of the Related Art

The electrical activity of neuronal and muscle cells are governed by the activity of sodium channels on the plasma membrane of such cells. Rapid entry of sodium ions into the cell through such a channel causes depolarization of the membrane and generation of an action potential. Entry of sodium ions through sodium channels in response to a voltage change on the plasma membrane in excitable cells plays a functional role in the excitation of neurons in the central nervous system and the peripheral nervous system.

Sodium channels are voltage-gated transmembrane proteins that form ion channels within the membrane and have been the target of significant pharmacologic study, due to their potential role in a variety of pathological conditions. These sodium channels are responsible for the cellular uptake of sodium during the transmission of an electrical signal in cell membranes. The channels are members of a multigene family of proteins and are typically composed of a number of subunits. Typically, the pore of the channel is formed by the α-subunit and there are four accessory β-subunits, termed β1, β2, β3 and β3.

The β-subunits are involved in the modulation of the activity of sodium channel but the α-subunit is all that is required for the channel to form a functional ion pore. Co-expression of the β-subunits with the α-subunit has been shown to produce a more positive membrane potential. Further not all of the β-subunits are required, for example, it has been shown that the β3-subunits alone is sufficient to cause an increase in sodium current (Qu et al., Mol. Cell. Neurosci., 18(5):570-80 (2001)).

The amino acid sequence of the sodium channel has been evolutionarily conserved. The channel is comprised of a signal polypeptide containing four internal repeats (domains I-IV). Each domain folds into six transmembrane α-helices or segments, of which five are hydrophobic and one is a highly-charged domain containing lysine and arginine residues (S4 segment). The highly-charged S4 segment is involved in the voltage gating properties of the sodium channel. The positively-charged side chains of the amino acids of the S4 segment are thought to be paired with the negatively-charged side chains of the other five segments such that upon membrane depolarization there is a shift in the position of one of the helices relative to the other resulting in an opening of the channel.

There are numerous variants of sodium channel α-subunit. These variants may be classified according to their sensitivity to tetrodotoxin (TTX). Those subunits that are inhibited by nanomolar quantities of TTX are classified as tetrodotoxin-sensitive channels, whereas those that require at least micromolar quantities of TTX for inhibition are referred to as tetrodotoxin-insensitive (1-5 micromolar). Those channels that require greater that 100 micromolar quantities of the TTX are termed tetrodotoxin-resistant. TTX is a toxin that blocks the conduction of nerve impulses along the axons and leads to paralysis. It binds to sodium channels and blocks the flow of sodium ions. It is believed that the positively-charged group of the toxin interacts with a negatively-charged carboxylate at the mouth of the channel on the extracellular side of the membrane thereby blocking the conductance of the pathway.

It has been noted that following nerve injury there is hyperexcitability (or an increased rate of spontaneous impulse firing in neurons) in peripheral sensory ganglia. It has been suggested that this hyperexcitability in neurons is due to altered sodium channel expression in some chronic pain syndromes (Tanaka et al., Neuroreport; 9 (6): 967-72 (1998)). Increased numbers of sodium channels leading to inappropriate, repetitive firing of the neurons have been reported in the tips of injured axons in various peripheral nervous tissues such as the DRG, which relay signals from the peripheral receptors to the central nervous system. Indeed, it has been noted that there is an increase in expression of an α1 $Na_v$ 1.3 subunit in axotomized DRG neurons together with elevated levels of α1 $Na_v$ 1.1 and α1 $Na_v$ 1.2 mRNAs (Waxman et al, Brain Res Mol Brain Res; 22 (1-4): 275-89 (1994)).

The peripheral input that drives pain perception is thought to depend upon the presence of functional voltage-gated sodium channels in peripheral nerves. It has been noted that there is a positive correlation between increased sodium channel expression in peripheral nerves. Some studies have also shown increased expression in association with neuropathic pain. In particular, it has been recognized that acute, inflammatory, and neuropathic pain can all be attenuated or abolished by local treatment with sodium channel blockers such as lidocaine. Remarkably, two voltage-gated sodium channel genes (NaV1.8 and Nav1.9) are expressed selectively in damage-sensing peripheral neurons, while a third channel (Nav1.7) is found predominantly in sensory and sympathetic neurons. An embryonic channel (NaV1.3) is also upregulated in damaged peripheral nerves and associated with increased electrical excitability in neuropathic pain states. Using antisense and knock-out studies, it has been shown that these sodium channels play a specialized role in pain pathways, and pharmacological studies (Wood et al., J Neurobiol., 61(1):55-71 (2004)).

Most patients with traumatic spinal cord injury (SCI) report moderate to severe chronic pain that is refractory, or only partially responsive, to standard clinical interventions (Balazy, Clin J Pain 8: 102-110 (1992); Turner et al., Arch Phys Med Rehabil 82: 501-509 (2001)). Experimental contusion SCI in rodents can produce long-lasting central neuropathic pain (Hulsebosch et al., J Neurotrauma 17: 1205-1217 (2000); Lindsey et al., Neurorehabil Neural Repair 14: 287-300 (2000); Hains et al., Neuroscience 116: 1097-1110 (2001); Mills et al., J Neurotrauma 18: 743-756 (2001)). In spinally injured animals, alterations in electrophysiologic properties of dorsal horn neurons (Hao et al., Pain 45: 175-185 (1991); Yezierski and Park, Neurosci Lett 157: 115-119 (1993); Drew et al., Brain Res 893: 59-69 (2001); Hains et al., Neuroscience 116: 1097-1110 (2003a); Hains et al., Brain Res 970: 238-241 (2003b)) are thought to contribute to changes in somatosensory responsiveness.

An analysis of human and chimp genomes reveals a difference of 1% between the two species. Mapping this critical difference could lead to important insights into functions of specific genes. NaV1.8 and NaV1.9 contain an amino acid sequence common to tetrodotoxin resistant Na+ channels and are localized in peripheral nociceptors. Recent patch-clamp experiments on dorsal root ganglion neurons from NaV1.8-knock-out mice unveiled an additional tetrodotoxin-resistant Na+ current. The demonstration of its dependence on NaV1.9 provides evidence for a specialized role of NaV1.9, together with NaV1.8, in pain sensation. (Ogata, N., and Ohishi, Y, Jpn J Pharmacol 88, 365-377 (2002)). Chronic axonal damage of sensory neurons often results in painful and dysaesthetic sensations. These positive sensory symptoms of peripheral nerve injury are produced by ectopic nerve impulses in the damaged neurons generated at the site of injury by sprouting axons (known as a neuroma) and also at the soma.

Sodium channels accumulate at the sites of sprouting after axonal damage (Devor, M., et al., J Neurosci 13, 1976-1992 (1993)) and pharmacological experiments reveal an important role for voltage-gated sodium channels in spontaneous electrogenesis in neuromas (Matzner, O., & Devor M., J Neurophysiol 72, 349-359 (1994)). A selective accumulation of NaV1.8 in injured nerve fibers in the rat (Novakovic et al., J Neurosci 18, 2174-2187 (1998)) and in damaged nerves and skin from patients with painful neuropathy (Coward et al., Pain 85, 41-50 (2000)) has been shown using subtype-specific antibodies. Further inhibiting the expression of NaV1.8 protein using antisense oligonucleotides reverses thermal and mechanical hyperalgesia produced by spinal nerve ligation in rats (Porreca et al., Proc Natl Acad Sci U S A 96, 7640-7644 (1999); Lai et al., Pain 95, 143-152 (2002)).

There are various sodium channels that remain to be characterized. Identification of such channels will facilitate further studies and identification and characterization of further isotype-specific antagonists of sodium channel blockers. Such sodium channel blockers or antagonists will be useful in the management of pain. Preferably, such analgesic agents are such that treatment of pain is facilitated without having deleterious side effects due to cardiac, central nervous system or neuromuscular complications.

The present invention is directed to a chimp sodium channel alpha subunit and methods and compositions for making and using the same. More specifically, one embodiment of the invention is directed to an isolated recombinant nucleic acid encoding a chimp sodium channel NaV1.8 polypeptide, wherein the polypeptide comprises a) a polypeptide sequence of SEQ ID NO: 2, b) a variant SEQ ID NO: 2 that is at least 90% identical to SEQ ID NO: 2 and has sodium channel activity; c) a NaV1.8 polypeptide that is encoded by a nucleic acid having the sequence of SEQ ID NO: 1, or d) a variant of SEQ ID NO: 2 encoded by a nucleic acid that hybridizes with a complementary strand of SEQ ID NO: 1 under stringent hybridization conditions wherein said variant has sodium channel activity. By "sodium channel activity" it is meant an activity associated with the uptake of sodium during the transmission of electrical signals in cell membranes.

The present invention is directed to a chimp sodium channel alpha subunit and methods and compositions for making and using the same. More specifically, one embodiment of the invention is directed to an isolated recombinant nucleic acid encoding a chimp sodium channel NaV1.8 polypeptide, wherein the polypeptide comprises a) a polypeptide sequence of SEQ ID NO: 2, b) a variant SEQ ID NO: 2 that is at least 90% identical to SEQ ID NO: 2 and has sodium channel activity; c) a NaV1.8 polypeptide that is encoded by a nucleic acid having the sequence of SEQ ID NO: 1, or d) a variant of SEQ ID NO: 2 encoded by a nucleic acid that hybridizes with a complementary strand of SEQ ID NO: 1 under stringent hybridization conditions wherein said variant has sodium channel activity. By "sodium channel activity" it is meant an activity associated with the uptake of sodium during the transmission of electrical signals in cell membranes.

Another embodiment of the invention describes an isolated recombinant nucleic acid encoding a chimp sodium channel NaV1.8 protein having the amino acid sequence of SEQ ID NO: 2. Also contemplated herein is an isolated recombinant nucleic acid comprising the sequence presented in SEQ ID NO: 1, the mature protein coding portion thereof, or a complement thereof. One preferred embodiment of the invention contemplates an isolated recombinant nucleic acid encoding a polypeptide of SEQ ID NO: 2. The nucleic acids described herein may be genomic DNA, cDNA, or RNA.

Another embodiment of the invention describes a compound 8 to 80 nucleotides in length targeted to a nucleic acid molecule encoding NaV1.8, wherein the compound specifically hybridizes with a nucleic acid molecule of SEQ ID NO: 1 and inhibits the expression of NaV1.8. In a related embodiment, the compound is 12 to 50, preferably 15 to 30, or more preferably 19 to 25 nucleotides in length.

In another embodiment, the compound is an antisense oligonucleotides, a DNA oligonucleotides, or an RNA oligonucleotide. In still another embodiment, at least a portion of the aforementioned compound hybridizes with RNA to form an oligonucleotide-RNA duplex. In yet another embodiment, the compound has at least 70%, at least 80%, at least 90%, or at least 95% complementarity with a nucleic acid molecule of SEQ ID NO 1 wherein said compound specifically hybridizes to and inhibits the expression of NaV1.8. In another embodiment, the compound has at least one modified internucleoside linkage, sugar moiety, or nucleotide.

Conservative variants of the sequences of the present invention are particularly contemplated, for example, the invention is directed to an isolated nucleic acid comprising a nucleotide sequence encoding a polypeptide that is a conservative variant of the amino acid sequences set forth in SEQ ID NO: 2, wherein the variant encodes a sodium channel $\alpha$-subunit.

Expression constructs that comprise an isolated nucleic acid encoding a protein having an amino acid sequence of SEQ ID NO: 2 or the mature protein portion thereof and a promoter operably linked to the polynucleotide also form part of the invention. In specific embodiments, the expression construct is such that the nucleic acid comprises a mature protein coding sequence of SEQ ID NO: 1. The expression construct is an expression construct selected from the group consisting of an adenoassociated viral construct, an adenoviral construct, a herpes viral expression construct, a vaccinia viral expression construct, a retroviral expression construct, a lentiviral expression construct and a naked DNA expression construct.

Also part of the invention are recombinant host cells stably transformed or transfected with a nucleic acid or an expression construct of the invention in a manner that allows the expression in the host cell of a protein of SEQ ID NO: 2. Preferably, the nucleic acid transforming the host cell comprises a mature protein encoding sequence of SEQ ID NO: 1. Recombinant host cells stably transformed or transfected with an expression construct of the invention in a manner allowing the expression in the host cell of a protein product of the expression construct also are contemplated.

The host cells may be mammalian, a bacterial, yeast cells, or insect cells. It may be advantageous that the recombinant host cells produced by the invention further express one or more $\beta$-subunits of a sodium channel selected from the group consisting of $\beta1$, $\beta2$, $\beta3$ and $\beta4$. In specific embodiments, the host cell is a HEK293 cell line.

The invention further provides an isolated and purified protein comprising an amino acid sequence of an amino acid sequence of SEQ ID NO: 2. In particular embodiments, the isolated and purified protein comprises an amino acid sequence that is 99% identical to the complete sequence of SEQ ID NO: 2. In other embodiments, the isolated and purified protein comprises an amino acid sequence that is 95% identical to the complete sequence of SEQ ID NO: 2.

The invention also comprises a diagnostic kit for detecting a nucleic acid that encodes a sodium channel α-subunit polypeptide, the polypeptide being encoded by the sequence of SEQ ID NO: 1 comprising an isolated nucleic acid probe complementary to the complete sequence of SEQ ID NO: 1, and means for containing the nucleic acid.

Methods of identifying a modulator of a chimp sodium channel α-subunit expression or activity are contemplated wherein the modulator is identified by a method comprising the steps of contacting a cell that expresses a nucleic acid of SEQ ID NO: 1 with the candidate modulator substance; monitoring the expression or ion channel activity of a protein of SEQ ID NO: 2; and comparing the expression or ion channel activity of a protein of SEQ ID NO: 2 in the presence and absence of the candidate substance; wherein an alteration in the expression or ion channel activity of a protein of SEQ ID NO: 2 indicates that the substance is a modulator of chimp sodium channel α-subunit expression or activity.

The modulator of chimp sodium channel α-subunit expression or activity may be a small molecule ion channel blocker or inhibitor, an oligonucleotide, an antisense oligonucleotide, a DNA oligonucleotide, an RNA oligonucleotide, an RNA oligonucleotide having at least a portion of the RNA oligonucleotide capable of hybridizing with RNA to form an oligonucleotide-RNA duplex, a chimeric oligonucleotide or an expression construct that produces a modulatory nucleic acid (e.g., siRNA) or polypeptide.

The invention also provides methods of identifying a test compound that binds to a sodium channel comprising providing a cell that expresses a sodium channel having a sequence of SEQ ID NO: 2; contacting the host cell with the test compound and determining the binding of the test compound to the sodium channel; and comparing the binding of the test compound to the host cell determined in step (b) to the binding of the test compound with a cell that does not express a sodium channel.

Also provided is an assay for identifying a test compound that modulates the activity of a sodium channel comprising providing a host cell that expresses a functional sodium channel comprising at least one polypeptide comprising the amino acid sequence of SEQ ID NO: 2; contacting the host cell with a test compound under conditions that would activate sodium channel activity of the functional sodium channel in the absence of the test compound; and determining whether the host cell contacted with the test compound exhibits a modulation in activity of the functional sodium channel. In particular embodiments, the host cell has been genetically engineered to express or overexpress the functional sodium channel. In other embodiments, the host cell has been genetically engineered by the introduction into the cell of a nucleic acid molecule having a nucleotide sequence encoding a polypeptide comprising the amino acid sequence of SEQ ID NO: 2. Preferably, the host cell has been genetically engineered to upregulate the expression of a nucleic acid encoding a polypeptide comprising the amino acid sequence of SEQ ID NO: 2. In particular embodiments, the upregulated nucleic acid is endogenous to the host cell. Preferably, the modulation of the functional sodium channel activity is an inhibition of that activity.

A method of producing a purified chimp sodium channel α-subunit protein also is provided, the method comprising preparing an expression construct comprising a nucleic acid of SEQ ID NO: 1 operably linked to a promoter; transforming or transfecting a host cell with the expression construct in a manner effective to allow the expression of a protein having an amino acid sequence of SEQ ID NO: 2, or the mature protein portion thereof in the host cell; culturing the transformed or transfected cell under conditions to allow the production of the protein by the transformed or transfected host cell; and isolating the chimp sodium channel α-subunit protein from the host cell.

Other embodiments contemplate treatment of a disorder by administering to a subject in need thereof a pharmaceutical composition that comprises a compound identified according to the methods described herein and a pharmaceutically acceptable carrier, excipient or diluent.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

DESCRIPTION OF THE PREFERRED EMBODIMENTS

The tetrodotoxin-resistant sodium channel subunit, NaV1.8, is exclusively expressed in primary sensory neurons and is suggested to play a role in the generation of ectopic action potentials after axonal injury and thereby contribute to neuropathic pain. Thus, therapies designed to knock-out or block the action of NaV1.8 are important in alleviating neuropathy. The present application is directed to the α1 subunit of chimp NaV1.8.

Based on the homology of human and chimp genomes, the full-length cDNA of the NaV1.8 sodium channel from chimp dorsal root ganglion was cloned. In addition, the exact position of 10 amino acid differences in the three-dimensional structure of the protein was identified and studied for their effect on the function of this important sodium channel. Methods and compositions for making and using the chimp NaV1.8 of the present invention are described in further detail below.

Polypeptides and Fragments Thereof

According to the present invention, there has been identified the gene encoding chimp NaV1.8. It is contemplated that these genes and the proteins encoded by the same may be used in studies of sodium channels and in the identification of modulators thereof. In this regard, it is noted that sodium channel α-subunits are well known to those of skill in the art and have been described e.g., in U.S. Pat. No. 6,479,259; U.S. Pat. No. 6,335,172; U.S. Pat. No. 6,184,349; U.S. Pat. No. 6,060,271; U.S. Pat. No. 6,030,810; U.S. Pat. No. 5,892,018; U.S. Pat. No. 5,776,859; U.S. Pat. No. 5,693,756; U.S. Pat. No. 5,437,982; U.S. Pat. No. 5,380,836. Each of the foregoing patents are incorporated herein by reference as providing specific teaching of how to make and use sodium channel proteins and nucleic acids that encode the same. The methods taught therein for using such compositions to identify therapeutic agents, e.g., sodium channel blockers or even β-subunits that are modulators of sodium channel a-subunits may readily be adapted using the protein and nucleic acid compositions of the present invention. As discussed above, NaV1.8 sodium channels are involved in mediating pain associated with neuronal injury. As such, it is contemplated that it will be will be desirable to inhibit, decrease, ablate, reduce or otherwise diminish the expression of the NaV1.8 gene or the activity of the protein product of the gene expression described herein. It is contemplated that inhibition of activity of the encoded protein or the expression of this gene will have a beneficial effect in treating pain. Inhibition of the gene expression may even be helpful in regenerative studies or overcoming the deleterious effects of spinal cord injury.

In the therapeutic aspects, guidance may be gained from the functional and therapeutic aspects of sodium channels described in e.g., in U.S. Pat. No. 6,479,259; U.S. Pat. No. 6,335,172; U.S. Pat. No. 6,184,349; U.S. Pat. No. 6,060,271; U.S. Pat. No. 6,030,810; U.S. Pat. No. 5,892,018; U.S. Pat. No. 5,776,859; U.S. Pat. No. 5,693,756; U.S. Pat. No. 5,437,982; U.S. Pat. No. 5,380,836 been recognized as being involved in pain and have been used as targets for therapy. Sodium channel blockers or modulators have been described e.g., in U.S. Pat. No. 6,756,400; U.S. Pat. No. 6,646,012; U.S. Pat. No. 6,613,345; U.S. Pat. No. 6,607,741; U.S. Pat. No. 6,559,154; U.S. Pat. No. 6,479,498 (each incorporated by reference) and such patents provide guidance as to methods and compositions for identification of additional such therapeutic agents once new targets such as the chimp NaV1.8 of the present invention, are identified. While treatment of pain and the like will involve inhibition or blocking of NaV1.8 activity, it is contemplated that in certain embodiments, it may be desirable to increase the expression of NaV1.8. For example, in specific embodiments, it would be desirable to increase, augment or otherwise supplement endogenous NaV1.8 expression and/or activity in commercial or experimental endeavors where it would be desirable to produce animal models or cells that have an increased NaV1.8 expression and are phenotypically models for neuropathic pain.

The chimp NaV1.8 has been cloned by the present inventors and are taught herein to have a nucleic acid sequence as shown in SEQ ID NO: 1. The amino acid sequence of chimp NaV1.8 is shown in SEQ ID NO: 2.

In addition to the entire chimp NaV1.8 of SEQ ID NO: 2, the compositions of the present invention also may employ fragments of the polypeptides of SEQ ID NO:2 that retain the ability/activity to form a sodium channel. Fragments, including the N-terminus or C-terminus of the molecule may be generated by genetic engineering of translation start or stop sites within the coding region (discussed below). Alternatively, treatment of the chimp NaV1.8 with proteolytic enzymes, (proteases), can produce a variety of N-terminal, C-terminal and internal fragments. Examples of fragments may include contiguous residues of the chimp NaV1.8 protein sequence of SEQ ID NO:2 of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, or more amino acids in length. Such fragments preferably retain one or more of the biological activities of NaV1.8 and/or retain an immunological (antigenic) property of NaV1.8 protein. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

When the present application refers to the function of NaV1.8 "wild-type" activity, it is meant that the molecule in question has the ability to form a sodium channel in a plasma membrane fraction. An assessment of the particular molecules that possess such activities may be achieved using standard assays familiar to those of skill in the art. For example, the immunological studies will readily reveal whether chimp NaV1.8 is bound by antibodies directed against chimp NaV1.8 or other sodium channel alpha subunits. Such antibodies are known to those of skill in the art and may be readily generated using routine methods.

In certain embodiments, chimp NaV1.8 analogs and variants may be prepared and will be useful in a variety of applications. Amino acid sequence variants of the polypeptide can be substitutional, insertional or deletion variants. Deletion variants lack one or more residues of the native protein which are not essential for function or immunogenic activity. A common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, also called fusion proteins, are discussed below.

Substitutional variants typically exchange one amino acid of the wild type for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In order to construct such mutants, one of skill in the art may employ well known standard technologies. Specifically contemplated are N-terminal deletions, C-terminal deletions, internal deletions, as well as random and point mutagenesis.

N-terminal and C-terminal deletions are forms of deletion mutagenesis that take advantage for example, of the presence of a suitable single restriction site near the end of the C- or N-terminal region. The DNA is cleaved at the site and the cut ends are degraded by nucleases such as BAL31, exonuclease III, DNase I, and S1 nuclease. Rejoining the two ends produces a series of DNAs with deletions of varying size around the restriction site. Alternatively, deletions can be generated using polymerase chain reaction (PCR) amplification of cDNAs using primers that exclude regions of the coding sequence corresponding to the desired polypeptide deletion. Proteins expressed from such mutants can be assayed for appropriate activity as voltage-gated sodium channels, as described throughout the specification. Similar techniques may be employed for internal deletion mutants by using two suitably placed restriction sites, thereby allowing a precisely defined deletion to be made, and the ends to be religated as above. Similarly, PCR can be used to amplify the sequences flanking the internal deletion and then ligation used as described above to generate the DNA clone containing the desired deletion.

Also contemplated are partial digestion mutants. In such instances, one of skill in the art would employ a "frequent cutter", which cuts the DNA in numerous places depending on the length of reaction time. Thus, by varying the reaction conditions it will be possible to generate a series of mutants of varying size, which may then be screened for activity.

A random insertional mutation may also be performed by cutting the DNA sequence with DNase I, for example, and inserting a stretch of nucleotides that encode, 3, 6, 9, 12 etc., amino acids and religating the end. Once such a mutation is made, the mutants can be screened for various activities presented by the wild-type protein.

Point mutagenesis also may be employed to identify with particularity which amino acid residues are important in particular activities associated with chimp NaV1.8. Thus, one of skill in the art will be able to generate single base changes in the DNA strand to result in an altered codon and a missense mutation.

The amino acids of a particular protein can be altered to create an equivalent, or even an improved, second-generation molecule. Such alterations contemplate substitution of a given amino acid of the protein without appreciable loss of interactive binding capacity with structures such as, for example, antigen-binding regions of antibodies or binding sites on substrate molecules or receptors. Since it is the interactive capacity and nature of a protein that defines that protein's biological functional activity, certain amino acid substitutions can be made in a protein sequence, and its underlying DNA coding sequence, and nevertheless obtain a protein with like properties. Thus, various changes can be made in the DNA sequences of genes without appreciable loss of their biological utility or activity, as discussed below. Codon tables that show the codons that encode particular amino acids are well known to those of skill in the art. In making changes to the sequences of SEQ ID NO: 2, the hydropathic index of amino acids may be considered, which contributes to the secondary structure of the resultant protein, which in turn defines the interaction of the protein with other molecules, for example, enzymes, substrates, receptors, DNA, antibodies, antigens, and the like (Kyte & Doolittle, J. Mol. Biol., 157(1):105-132 (1982), incorporated herein by reference). Generally, amino acids may be substituted by other amino acids that have a similar hydropathic index or score and still result in a protein with similar biological activity, i.e., still obtain a biological functionally equivalent protein. Hydrophilicity is another parameter that may be used to determine amino acid substitution (see e.g., U.S. Pat. No. 4,554,101).

Exemplary amino acid substitutions that may be used in this context of the invention include but are not limited to exchanging arginine and lysine; glutamate and aspartate; serine and threonine; glutamine and asparagine; and valine, leucine and isoleucine. Other such substitutions that take into account the need for retention of some or all of the biological activity whilst altering the secondary structure of the protein will be well known to those of skill in the art.

Another type of variant that is specifically contemplated for the preparation of polypeptides according to the invention is the use of peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outlined above, to engineer second generation molecules having many of the natural properties of chimp NaV1.8, but with altered and even improved characteristics.

Other mutants that are contemplated are those in which entire domains of the chimp NaV1.8 are switched with those of another related protein. For example, other sodium channels exist and chimeric sodium channels may be produced where domains from e.g., a NaV1.3 protein are switched with domains from the chimp NaV1.8. Domain switching is well-known to those of skill in the art and is particularly useful in generating mutants having domains from related species.

Domain switching involves the generation of chimeric molecules using different but related polypeptides. For example, by comparing the sequence of chimp NaV1.8 with that of similar sequences from another source and with mutants and allelic variants of these polypeptides, one can make predictions as to the functionally significant regions of these molecules. Thus, it is contemplated then to switch related domains of these molecules in an effort to determine the criticality of these regions to chimp NaV1.8 function. These molecules may have additional value in that these "chimeras" can be distinguished from natural molecules, while possibly providing the same or even enhanced function.

In addition to the mutations described above, the present invention further contemplates the generation of a specialized kind of insertional variant known as a fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

There are various commercially available fusion protein expression systems that may be used in the present invention. Particularly useful systems include but are not limited to the glutathione S-transferase (GST) system (Pharmacia, Piscataway, N.J.), the maltose binding protein system (NEB, Beverley, Mass.), the FLAG system (IBI, New Haven, Conn.), and the 6×His system (Qiagen, Chatsworth, Calif.). These systems are capable of producing recombinant polypeptides bearing only a small number of additional amino acids, which are unlikely to affect the antigenic ability of the recombinant polypeptide. For example, both the FLAG system and the 6×His system add only short sequences, both of which are known to be poorly antigenic and which do not adversely affect folding of the polypeptide to its native conformation. Another N-terminal fusion that is contemplated to be useful is the fusion of a Met Lys dipeptide at the N-terminal region of the protein or peptides. Such a fusion may produce beneficial increases in protein expression or activity.

A particularly useful fusion construct may be one in which a chimp NaV1.8 of the present invention is fused to a hapten to enhance immunogenicity of a chimp NaV1.8 fusion construct. Such fusion constructs to increase immunogenicity are well known to those of skill in the art, for example, a fusion of chimp NaV1.8 with a helper antigen such as hsp70 or peptide sequences such as from Diptheria toxin chain or a cytokine such as IL-2 will be useful in eliciting an immune response. In other embodiments, fusion construct can be made which will enhance the targeting of the chimp NaV1.8-related compositions to a specific site or cell.

Other useful fusions include chimp NaV1.8 protein fused to specific peptide or polypeptide domains that serve to increase cell surface expression of membrane proteins. Examples of such domains include one known to increase the cell surface expression of potassium channels by facilitating exit from the endoplasmic reticulum (see Zerangue et al., Neuron 22: 537-548 (1999)).

Other fusion constructs including a heterologous polypeptide with desired properties also are contemplated. Other fusion systems produce polypeptide hybrids where it is desirable to excise the fusion partner from the desired polypeptide. In one embodiment, the fusion partner is linked to the recombinant chimp NaV1.8 polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

It will be desirable to purify chimp NaV1.8 or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure polypeptide are ion-exchange chromatography, exclusion chromatography; polyacrylamide gel electrophoresis; isoelectric focusing; affinity columns specific for protein fusion moieties; affinity columns containing chimp NaV1.8-specific or chimp NaV1.8-specific antibodies. A particularly efficient method of purifying polypeptides is fast protein liquid chromatography or even HPLC.

Certain aspects of the present invention concern the purification, and in particular embodiments, the substantial purification, of an encoded protein or polypeptide. The term "purified protein or polypeptide" as used herein, is intended to refer to a composition, isolatable from other components, wherein the protein or polypeptide is purified to any degree relative to its naturally-obtainable state. A purified protein or peptide therefore also refers to a protein or peptide, free from the environment in which it may naturally occur. As is common with purification of transmembrane proteins such as ion channels, it is possible that the purified protein may need to be incorporated in synthetic liposomes to retain biological activity.

Incorporation of proteins into liposomes is well known to those of skill in the art. The most frequently used strategy for reconstitution and crystallization of transmembrane proteins in lipid bilayers is co-micellization of the proteins and lipids, both solubilized with detergent, which is removed after mixing the separate solutions (e.g., Jap et al., Ultramicroscopy, 46:45-84 (1992); Kühlbrandt, Q. Rev. Biophys., 25:1-49 (1992); Rigaud et al., Struct. Biol., 118:226-235 (1995); Mosser, Micron., 32:517-540 (2001)). Additional chemical agents are usually added to the solution, including e.g., detergents such as octyl thioglucoside (Scheuring et al., EMBO J., 20:3029-3035 (2001)), octyl glucoside, octyl glucopyranoside (Montoya et al., J. Mol. Biol., 250:1-10 (1995)), organic solvents such as pentane, hexane, or other chemicals such as glucose (Walz et al., J. Mol. Biol., 282:833-845 (1998)) or glycerol (Ikeda-Yamasaki et al., FEBS Lett., 425:505-508 (1998)). The concentration of the detergent molecules in these solutions is then gradually reduced, either by dialysis or by the addition of Bio-Beads (Rigaud et al., J. Struct. Biol., 118:226-235 (1997)). As the concentration of the detergent decreases from these lipid-detergent and lipid-protein-detergent micellar solutions, lipid bilayers are progressively formed in which the transmembrane proteins are incorporated. Usually, the morphology of the resulting 2D crystals depends on several poorly defined factors, and depending on the circumstances, various structures can be obtained such as planar sheets, proteo-liposomes, multilayered stacked sheets, thin three-dimensional crystals, and tubes (Lacapere et al., Biophys. J., 75:1319-1329 (1998); Mosser, Micron., 32:517-540 (2001)). Specifically contemplated compositions of the present invention include the chimp NaV1.8 splice variants of the present invention incorporated into a liposomal preparation using techniques such as those outlined above. The splice variant protein compositions for incorporation into the liposomes may be prepared and purified using any standard protein preparation techniques.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE. It will therefore be appreciated that under differing electrophoresis conditions, the apparent molecular weights of purified or partially purified expression products may vary.

In addition to the chimp NaV1.8 of SEQ ID NO: 2 described herein, smaller chimp NaV1.8-related peptides derived from the sequence of SEQ ID NO: 2 may be useful in various embodiments of the present invention. Such peptides or indeed even the full length protein, of the invention can also be synthesized in solution or on a solid support in accordance with conventional techniques. Various automatic synthesizers are commercially available and can be used in accordance with known protocols. See, for example, Stewart and Young, Solid Phase Peptide Synthesis, 2d. ed., Pierce Chemical Co. (1984); Tam et al., J. Am. Chem. Soc., 105:6442 (1983); Merrifield, *Science,* 232: 341-347 (1986); and Barany and Merrifield, The Peptides, Gross and Meienhofer, eds, Academic Press, New York, 1-284 (1979), each incorporated herein by reference. The chimp NaV1.8 or portions of the mutants, which correspond to the selected regions described herein, can be readily synthesized and then screened in screening assays designed to identify reactive peptides.

Alternatively, recombinant DNA technology may be employed wherein a nucleotide sequence which encodes a peptide of the invention is inserted into an expression vector, transformed or transfected into an appropriate host cell and cultivated under conditions suitable for expression as described herein below.

U.S. Pat. No. 4,554,101 (incorporated herein by reference) also teaches the identification and preparation of epitopes from primary amino acid sequences on the basis of hydrophilicity. Thus, one of skill in the art would be able to identify epitopes from within any amino acid sequence encoded by any of the DNA sequences disclosed herein.

The protein of SEQ ID NO: 2 or proteins and peptides derived therefrom, may be useful as antigens for the immunization of animals relating to the production of antibodies. It is envisioned that such protein, or portions thereof, may be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

Chimp NaV1.8 Encoding Nucleic Acids

The present invention also provides, in another embodiment, an isolated nucleic acid encoding the chimp NaV1.8 of the invention. Preferred embodiments of the present invention are directed to nucleic acid constructs comprising a sequence of SEQ ID NO: 1. Preferably, the sequence is operably linked to a heterologous promoter. The present invention is not limited in scope to the particular gene(s) identified herein, however, seeing as one of ordinary skill in the art could, using the nucleic acids corresponding to the chimp NaV1.8, readily identify related homologs in various other species (e.g., human, rat, rabbit, monkey, gibbon, ape, baboon, cow, pig, horse, sheep, cat and other species). By way of example, reference is made to co-filed U.S. application Ser. No. 11/540,143 which discloses human NaV1.8 deletion mutant nucleotide and amino acid sequences.

In addition, it should be clear that the present invention is not limited to the specific nucleic acids disclosed herein. As discussed below, a "chimp NaV1.8 gene" may contain a variety of different nucleic acid bases and yet still produce a corresponding polypeptide that is functionally indistinguishable, and in some cases structurally, from the chimp gene disclosed herein. In preferred embodiments, the nucleic acid encodes SEQ ID NO: 2. In other embodiments the nucleic acids encode a function sodium channel alpha subunit based on the amino acid sequences of SEQ ID NO: 2. The term "chimp NaV1.8 gene" may be used to refer to any nucleic acid that encodes such a protein, peptide or polypeptide and, as such, is intended to encompass both genomic DNA, mRNA and cDNA.

Similarly, any reference to a nucleic acid should be read as encompassing a host cell containing that nucleic acid and, in some cases, capable of expressing the product of that nucleic acid. Such cells expressing nucleic acids of the present invention are contemplated to be particularly useful in the context of screening for agents that induce, repress, inhibit, augment, interfere with, block, abrogate, stimulate or enhance the function of chimp NaV1.8 gene or protein product. Such compounds identified in these screening assay embodiments also will be useful as sodium channel modulators of other sodium channels (e.g., NaV1.3, NaV1.6 and the like).

Nucleic acids according to the present invention (which include genomic DNA, cDNA, mRNA, as well as recombinant and synthetic sequences and partially synthetic sequences) may encode an entire chimp NaV1.8 of SEQ ID NO: 2, or polypeptide, or allelic variant, a domain of the protein that expresses an activity of the wild-type sodium channel, or any other fragment or variant of the chimp NaV1.8 sequences set forth herein.

The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that due to the redundancy of the genetic code, a given NaV1.8 gene from a given species may be represented by degenerate variants that have slightly different nucleic acid sequences but, nonetheless, encode the same protein.

As used in this application, the term "a nucleic acid encoding a chimp NaV1.8 protein" refers to a nucleic acid molecule that has been genetically modified following isolation from total cellular nucleic acid. In preferred embodiments, the invention concerns a nucleic acid sequence essentially as set forth in SEQ ID NO: 1. The term "functionally equivalent codon" is used herein to refer to codons that encode the same amino acid, such as the six codons for arginine or serine (Table 1, below), and also refers to codons that encode biologically equivalent amino acids, as discussed in the following pages.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Nucleotide sequences that have at least about 95% of nucleotides that are identical to the nucleotides of the entire sequence of SEQ ID NO: 1 are preferred. Sequences that are essentially the same as those set forth in SEQ ID NO: 1 may also be functionally defined as sequences that are capable of hybridizing to a nucleic acid segment containing the complement of SEQ ID NO: 1 under standard conditions.

The DNA segments of the present invention include those encoding biologically functional equivalent chimp NaV1.8 and peptides as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through any means described herein or known to those of skill in the art.

The present invention also encompasses DNA segments that are complementary, or essentially complementary, to the sequence set forth in SEQ ID NO: 1. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO: 1 under highly stringent conditions. Such sequences may encode the entire chimp NaV1.8 of SEQ ID NO: 2 or functional or non-functional fragments thereof.

Alternatively, the hybridizing segments may be shorter oligonucleotides. Sequences of about 17 bases long should occur only once in the chimp genome and, therefore, suffice to specify a unique target sequence. Antisense nucleic acids directed against the sequence of SEQ ID NO: 1 are particularly useful.

Suitable hybridization conditions will be well known to those of skill in the art. In certain applications, it is appreciated that lower stringency conditions may be required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C. Formamide and SDS also may be used to alter the hybridization conditions.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids also are routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement. Site-directed mutagenesis can also be accomplished using PCR to introduce the desired alteration in the coding sequence. In this case, one of the amplification primers contains the alteration(s) of choice and results in a DNA fragment containing the desired mutation(s) that can then be incorporated into the full-length construct.

Of course site-directed mutagenesis is not the only method of generating potentially useful mutant protein species and as such is not meant to be limiting. The present invention also contemplates other methods of achieving mutagenesis such as for example, treating the recombinant vectors carrying the gene of interest mutagenic agents, such as hydroxylamine, to obtain sequence variants.

It will be useful to inhibit the expression of NaV1.8 to decrease the activity of the encoded protein and effect and ameliorative outcome on pain. One may advantageously disrupt the activity or expression of a protein using a variety of methods known to those of skill in the art. For example, nucleic acid-based methods of disrupting or blocking NaV1.8 expression are contemplated. Polynucleotide products which are useful in this endeavor include antisense polynucleotides, ribozymes, RNAi, and triple helix polynucleotides that modulate the expression of NaV1.8.

Antisense polynucleotides and ribozymes are well known to those of skill in the art. Crooke and B. Lebleu, eds. Antisense Research and Applications (1993) CRC Press; and Antisense RNA and DNA (1988) D. A. Melton, Ed. Cold Spring Harbor Laboratory Cold Spring Harbor, N.Y. Antisense RNA and DNA molecules act to directly block the translation of mRNA by binding to targeted mRNA and preventing protein translation. An example of an antisense polynucleotide is an oligodeoxyribonucleotide derived from the translation initiation site, e.g., between −10 and +10 regions of the relevant nucleotide sequence.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozymes) could be designed. These molecules, though having less than 50% homology, would bind to target sequences under appropriate conditions.

Small interfering RNAs (siRNAs) are also contemplated by the present invention. The term "siRNA" refers to nucleotides of approximately 19-25 bases in length which incorporate into an RNA-induced silencing complex in order to guide the complex to homologous endogenous mRNA for cleavage and degradation of Nav1.8 mRNA. RNA interference (RNAi) is initiated by the conversion of dsRNA into 19-25 nucleotide fragments and these siRNAs direct the degradation of target RNAs. (Elbashir et al., Nature, 411, 494-498 (2001), Fire et al., Nature, 391, 199-213 (1998), Hannon, G. J., Nature, 418, 244-251 (2002)). siRNAs have been adopted to use for silencing genes in a variety of biological systems. (Reich et al., Mol. Vis., 9, 210-216 (2003), Song et al., Nat. Med., 9, 347-351 (2003))

RNAi technology may be carried out in mammalian cells by transfection of siRNA molecules. The siRNA molecules may be chemically synthesized, generated by in vitro transcription, or expressed by a vector or PCR product. Commercial providers such as Ambion Inc. (Austin, Tex.), Darmacon Inc. (Lafayette, Colo.), InvivoGen (San Diego, Calif.), and Molecular Research Laboratories, LLC (Herndon, Va.) generate custom siRNA molecules. In addition, commercial kits are available to produce custom siRNA molecules, such as SILENCER™ siRNA Construction Kit (Ambion Inc., Austin, Tex.) or psiRNA System (InvivoGen, San Diego, Calif.). These siRNA molecules may be introduced into cells through transient transfection or by introduction of expression vectors that continually express the siRNA in transient or stably transfected mammalian cells. Transfection may be accomplished by well known methods including methods such as infection, calcium chloride, electroporation, microinjection, lipofection or the DEAE-dextran method or other known techniques. These techniques are well known to those of skill in the art.

The siRNA molecules may be introduced into a cell in vivo by local injection of or by other appropriate viral or non-viral delivery vectors. Hefti, Neurobiology, 25:1418-1435 (1994). Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Methods of introducing the siRNA molecules may also include the use of inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture.

The preferred siRNA molecule is 19-25 base pairs in length, most preferably 21-23 base pairs, and is complementary to the target gene sequence. The siRNA molecule preferably has two adenines at its 5' end, but may not be an absolute requirement. The siRNA sequences that contain 30-50% guanine-cytosine content are known to be more effective than sequences with a higher guanine-cytosine content. Therefore, siRNA sequence with 30-50% are preferable, while sequences with 40-50% are more preferable. The preferred siRNA sequence also should not contain stretches of 4 or more thymidines or adenines.

By way of example, SEQ ID NO: 1 is 5,871 nucleotides in length. A series of siRNA molecules of 19-25 nucleotides in length are designed to correspond to 19-25 nucleotide fragments of SEQ ID NO: 1. Typically, a large number of candidate antisense oligonucleotides (ASOs) are synthesized having sequences that are more-or-less randomly spaced across the length of the target nucleic acid sequence (e.g., a "gene walk") and their ability to modulate the expression of the target nucleic acid is assayed. As used herein, the term "gene walk" is defined as the process by which a specified oligonucleotide sequence X that binds to a specified nucleic acid target Y (e.g., SEQ ID NO: 1) is used as a frame of reference around which a series of new oligonucleotides sequences capable of hybridizing to nucleic acid target Y are generated that are frame shift increments of oligonucleotide sequence X.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

As indicated above, the DNA and protein sequences for the specific chimp NaV1.8 of the present invention are provided in SEQ ID NO: 1 and SEQ ID NO: 2, respectively. Related protein and/or nucleic acid sequences from other sources may be identified using probes directed at the sequences of SEQ ID NO: 1. Such additional sequences may be useful in certain aspects of the present invention. Although antisense sequences may be full length genomic or cDNA copies, they also may be shorter fragments or oligonucleotides e.g., polynucleotides of 100 or less bases. Although shorter oligomers (8-20) are easier to make and more easily permeable in vivo, other factors also are involved in determining the specificity of base pairing. For example, the binding affinity and sequence specificity of an oligonucleotide to its complementary target increases with increasing length. It is contemplated that oligonucleotides of 8, 9, 10, 11, 12, 13, 14, 15, 16, 17, 18, 19, 20, 25, 30, 35, 40, 45, 50, or more base pairs will be used.

Ribozymes are enzymatic RNA molecules capable of catalyzing the specific cleavage of RNA. The mechanism of ribozyme action involves sequence specific interaction of the ribozyme molecule to complementary target RNA, followed by an endonucleolytic cleavage. Within the scope of the invention are engineered hammerhead or other motif ribozyme molecules that specifically and efficiently catalyze endonucleolytic cleavage of RNA sequences encoding protein complex components.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using ribonuclease protection assays. See, Draper PCT WO 93/23569; and U.S. Pat. No. 5,093,246.

Nucleic acid molecules used in triple helix formation for the inhibition of transcription are generally single stranded and composed of deoxyribonucleotides. The base composition must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC+ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Another technique that is of note for reducing or disrupting the expression of a gene is RNA interference (RNAi), also known as small interfering RNA (siRNA). The term "RNA interference" was first used by researchers studying *C. elegans* and describes a technique by which post-transcriptional gene silencing (PTGS) is induced by the direct introduction of double stranded RNA (dsRNA: a mixture of both sense and antisense strands). Injection of dsRNA into *C. elegans* resulted in much more efficient silencing than injection of either the sense or the antisense strands alone (Fire et al., Nature 391:806-811, 1998). Just a few molecules of dsRNA per cell is sufficient to completely silence the expression of the homologous gene. Furthermore, injection of dsRNA caused gene silencing in the first generation offspring of the *C. elegans* indicating that the gene silencing is inheritable (Fire et al., Nature 391:806-811 (1998)). Current models of PTGS indicate that short stretches of interfering dsRNAs (21-23 nucleotides; siRNA also known as "guide RNAs") mediate PTGS. siRNAs are apparently produced by cleavage of dsRNA introduced directly or via a transgene or virus. These siRNAs may be amplified by an RNA-dependent RNA polymerase (RdRP) and are incorporated into the RNA-induced silencing complex (RISC), guiding the complex to the homologous endogenous mRNA, where the complex cleaves the transcript. Thus, siRNAs are nucleotides of a short length (typically 18-25 bases, preferably 19-23 bases in length) which incorporate into an RNA-induced silencing complex in order to guide the complex to homologous endogenous mRNA for cleavage and degradation of the transcript.

While most of the initial studies were performed in *C. elegans*, RNAi is gaining increasing recognition as a technique that may be used in mammalian cell. It is contemplated that RNAi, or gene silencing, will be particularly useful in the disruption of tissue-specific gene expression. By placing a gene fragment encoding the desired dsRNA behind an inducible or tissue-specific promoter, it should be possible to inactivate genes at a particular location within an organism or during a particular stage of development.

Variations on RNA interference (RNAi) technology is revolutionizing many approaches to experimental biology, complementing traditional genetic technologies, mimicking the effects of mutations in both cell cultures and in living animals. (McManus & Sharp, Nat. Rev. Genet., 3, 737-747 (2002)). RNAi has been used to elicit gene-specific silencing in cultured mammalian cells using 21-nucleotide siRNA duplexes (Elbashir et al., Nature, 411:494-498 (2001); Fire et al., Nature, 391: 199-213 (1998); Hannon, G. J., Nature, 418: 244-251 (2002)). In the same cultured cell systems, transfection of longer stretches of dsRNA yielded considerable non-specific silencing. Thus, RNAi has been demonstrated to be a feasible technique for use in mammalian cells and could be used for assessing gene function in cultured cells and mammalian systems, as well as for development of gene-specific therapeutics. In particularly preferred embodiments, the siRNA molecule is between 20 and 25 oligonucleotides in length and is derived from the sequence of SEQ ID NO: 1. Particularly preferred siRNA molecules are 21-23 bases in length.

Anti-sense RNA and DNA molecules, ribozymes, RNAi and triple helix molecules can be prepared by any method known in the art for the synthesis of DNA and RNA molecules. These include techniques for chemically synthesizing oligodeoxyribonucleotides well known in the art including, but not limited to, solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably or transiently into cells.

Commercial providers such as Ambion Inc. (Austin, Tex.), Darmacon Inc. (Lafayette, Colo.), InvivoGen (San Diego, Calif.), and Molecula Research Laboratories, LLC (Herndon, Va.) generate custom siRNA molecules. In addition, commercial kits are available to produce custom siRNA molecules, such as SILENCER™ siRNA Construction Kit (Ambion Inc., Austin, Tex.) or psiRNA System (InvivoGen, San Diego, Calif.). These siRNA molecules may be introduced into cells through transient transfection or by introduction of expression vectors that continually express the siRNA in transient or stably transfected mammalian cells. Transfection may be accomplished by well known methods including methods such as infection, calcium chloride, electroporation, microinjection, lipofection or the DEAE-dextran method or other known techniques. These techniques are well known to those of skill in the art.

Recombinant Protein Production

Given the above disclosure of SEQ ID NO: 1, it is possible to produce protein of SEQ ID NO: 2 and by recombinant techniques. A variety of expression vector/host systems may be utilized to contain and express such a protein coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant protein production include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of a protein of amino acid sequence of SEQ ID NO: 2 in bacteria, yeast and other invertebrates are described herein below.

The DNA sequence encoding the mature form of the protein is amplified by PCR and cloned into an appropriate vector for example, pGEX 3× (Pharmacia, Piscataway, N.J.). The pGEX vector is designed to produce a fusion protein comprising glutathione S transferase (GST), encoded by the vector, and a protein encoded by a DNA fragment inserted into the vector's cloning site. The primers for the PCR may be generated to include for example, an appropriate cleavage site.

Knowledge of SEQ ID NO: 1 allows for modification of cells to permit or increase expression of endogenous chimp NaV1.8 of the present invention. The cells can be modified (heterologous promoter is inserted in such a manner that it is operably linked to, e.g., by homologous recombination) to provide increased protein expression by replacing, in whole or in part the naturally occurring promoter with all or part of a heterologous promoter so that the cells express such a protein at higher levels. The heterologous promoter is inserted in such a manner that it is operably linked to a sequence of SEQ ID NO: 1. (e.g., PCT International Publication No. WO96/12650; PCT International Publication No. WO 92/20808 and PCT International Publication No. WO 91/09955). It is contemplated that, in addition to the heterologous promoter DNA, amplifiable marker DNA (e.g., ada, dhfr and the multifunctional CAD gene which encodes carbamyl phosphate synthase, aspartate transcarbamylase and dihydroorotase) and/or intron DNA may be inserted along with the heterologous promoter DNA. If linked to the gene sequence, amplification of the marker DNA by standard selection methods results in co-amplification of the chimp NaV1.8 with the marker sequence in the cells.

While certain embodiments of the present invention contemplate producing the chimp NaV1.8 using synthetic peptide synthesizers and subsequent FPLC analysis and appropriate refolding of the cysteine double bonds, it is contemplated that recombinant protein production also may be used. For example, induction of the fusion protein containing the protein of interest fused to GST is achieved by growing the transformed XL 1 Blue culture at 37° C. in LB medium (supplemented with carbenicillin) to an optical density at wavelength 600 nm of 0.4, followed by further incubation for 4 hours in the presence of 0.5 mM Isopropyl β-D Thiogalactopyranoside (Sigma Chemical Co., St. Louis Mo.).

The fusion protein, expected to be produced as an insoluble inclusion body in the bacteria, may be purified using standard techniques in which cells are harvested, washed, lysed and the protein extracted and purified e.g., using the GST Purification Module (Pharmacia Biotech). The GST may be cleaved using thrombin digestion.

The recombinant protein also may be prepared using a yeast system e.g., the Pichia Expression System (Invitrogen, San Diego, Calif.), following the manufacturer's instructions. Alternatively, the cDNA encoding the given chimp NaV1.8 may be cloned into the baculovirus expression vector pVL1393 (PharMingen, San Diego, Calif.). This vector is then used according to the manufacturer's directions (PharMingen) to infect *Spodoptera frugiperda* cells in sF9 protein free media and to produce recombinant protein. The protein is purified and concentrated from the media using a heparin Sepharose column (Pharmacia, Piscataway, N.J.) and sequential molecular sizing columns (Amicon, Beverly, Mass.), and resuspended in PBS. SDS PAGE analysis shows a single band and confirms the size of the protein, and Edman sequencing on a Porton 2090 Peptide Sequencer confirms its N-terminal sequence. In still other alternatives, an insect system expression system may be used.

Mammalian host systems for the expression of the recombinant protein also are well known to those of skill in the art and are most preferred. Host cell strains may be chosen for a particular ability to process the expressed protein or produce certain post translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

It is preferable that the transformed cells are used for long-term, high-yield protein production and as such stable expression is desirable. Once such cells are transformed with vectors that contain selectable markers along with the desired expression cassette, the cells may be allowed to grow for 1-2 days in an enriched media before they are switched to selective media. The selectable marker is designed to confer resistance to selection and its presence allows growth and recovery of cells which successfully express the introduced sequences. Resistant clumps of stably transformed cells can be proliferated using tissue culture techniques appropriate to the cell.

A number of selection systems may be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to methotrexate; gpt, that confers resistance to mycophenolic acid; neo, that confers resistance to the aminoglycoside G418; als which confers resistance to chlorsulfuron; and hygro, that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, glucuronidase and its substrate, GUS, and luciferase and its substrate, luciferin.

Vectors for Cloning, Gene Transfer and Expression

As discussed in the previous section, expression vectors are employed to express the protein of interest, which can then be purified and, for example, be used to vaccinate animals to generate antisera or monoclonal antibody with which further studies may be conducted.

Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products also are provided, as is an element that links expression of the drug selection markers to expression of the polypeptide.

Throughout this application, the term "expression construct" or "expression vector" is meant to include any type of genetic construct containing a nucleic acid coding for gene products in which part or all of the nucleic acid encoding sequence is capable of being transcribed. The transcript may be translated into a protein, but it need not be. In certain embodiments, expression includes both transcription of a gene and translation of mRNA into a gene product.

The nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. Exemplary promoters include the human cytomegalovirus (CMV) immediate early gene promoter, the SV40 early promoter, the Rous sarcoma virus long terminal repeat, β-actin, rat insulin promoter, the phosphoglycerol kinase promoter and glyceraldehyde-3-phosphate dehydrogenase promoter, all of which are promoters well known and readily available to those of skill in the art, can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well known properties, the level and pattern of expression of the protein of interest following transfection or transformation can be optimized. Inducible promoters e.g., inducible ecdysone system (Invitrogen, Carlsbad, Calif.), or the Tet-Off™ or Tet-On™ system which are designed to allow regulated expression of a gene of interest in mammalian cells also may be used.

Modified versions of the CMV promoter that are less potent have also been used when reduced levels of expression of the transgene are desired. When expression of a transgene in hematopoietic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Tissue specific promoters may be used to effect transcription in specific tissues or cells so as to reduce potential toxicity or undesirable effects to non-targeted tissues.

It is envisioned that any of the above promoters alone or in combination with another may be useful according to the present invention depending on the action desired. In addition, this list of promoters should not be construed to be exhaustive or limiting, and those of skill in the art will know of other promoters that may be used in conjunction with the promoters and methods disclosed herein.

Another regulatory element contemplated for use in the present invention is an enhancer. These are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization. Enhancers useful in the present invention are well known to those of skill in the art and will depend on the particular expression system being employed (Scharf, D., et al, Results Probl. Cell Differ., 20: 125-62 (1994); Bittner et al., Methods in Enzymol, 153: 516-544 (1987)).

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read through from the cassette into other sequences.

In certain embodiments of the invention, the use of internal ribosome entry site (IRES) elements is contemplated to create multigene, or polycistronic, messages. In specific embodiments herein it is contemplated that host cells are created which comprise both a chimp NaV1.8 alpha subunit and one or more beta subunits. IRES elements can be linked to heterologous open reading frames for such endeavors. IRES elements are able to bypass the ribosome scanning model of 5' methylated Cap dependent translation and begin translation at internal sites (Pelletier and Sonenberg, Nature, 334:320-325 (1988)). IRES elements from two members of the picornavirus family (poliovirus and encephalomyocarditis) have been described (Pelletier and Sonenberg, (1988 supra)), as well as IRES from a mammalian message (Macejak and Sarnow, Nature, 353:90-94 (1991)). Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

There are a number of ways in which expression constructs may be introduced into cells. In certain embodiments of the invention, the expression construct comprises a virus or engineered construct derived from a viral genome. In other embodiments, non-viral delivery such as lipid- or chemical-mediated transfection is contemplated. The ability of certain viruses to enter cells via receptor-mediated endocytosis, to integrate into host cell genome and express viral genes stably and efficiently have made them attractive candidates for the transfer of foreign genes into mammalian cells (Ridgeway, In: Rodriguez R L, Denhardt D T, ed. Vectors: A survey of molecular cloning vectors and their uses. Stoneham: Butterworth, 467-492 (1988); Nicolas and Rubenstein, In: Vectors: A survey of molecular cloning vectors and their uses, Rodriguez & Denhardt (eds.), Stoneham: Butterworth, 493-513 (1988); Baichwal and Sugden, In: Gene Transfer, Kucherlapati R, ed., New York, Plenum Press, 117-148 (1986); Temin, In: gene Transfer, Kucherlapati (ed.), New York: Plenum Press, 149-188 (1986)). The first viruses used as gene vectors were DNA viruses including the papovaviruses (simian virus 40, bovine papilloma virus, and polyoma) (Ridgeway (1988) supra; Baichwal and Sugden (1986) supra) and adenoviruses (Ridgeway (1988) supra; Baichwal and Sugden (1986) supra). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein (1988) supra; Temin (1986) supra).

It is now widely recognized that DNA may be introduced into a cell using a variety of viral vectors. In such embodiments, expression constructs comprising viral vectors containing the genes of interest may be adenoviral (see for example, U.S. Pat. No. 5,824,544; U.S. Pat. No. 5,707,618; U.S. Pat. No. 5,693,509; U.S. Pat. No. 5,670,488; U.S. Pat. No. 5,585,362; each incorporated herein by reference), retroviral (see for example, U.S. Pat. No. 5,888,502; U.S. Pat. No. 5,830,725; U.S. Pat. No. 5,770,414; U.S. Pat. No. 5,686,278; U.S. Pat. No. 4,861,719 each incorporated herein by reference), adeno-associated viral (see for example, U.S. Pat. No. 5,474,935; U.S. Pat. No. 5,139,941; U.S. Pat. No. 5,622,856; U.S. Pat. No. 5,658,776; U.S. Pat. No. 5,773,289; U.S. Pat. No. 5,789,390; U.S. Pat. No. 5,834,441; U.S. Pat. No. 5,863,541; U.S. Pat. No. 5,851,521; U.S. Pat. No. 5,252,479 each incorporated herein by reference), an adenoviral-adenoassociated viral hybrid (see for example, U.S. Pat. No. 5,856,152 incorporated herein by reference) or a vaccinia viral or a herpesviral (see for example, U.S. Pat. No. 5,879,934; U.S. Pat. No. 5,849,571; U.S. Pat. No. 5,830,727; U.S. Pat. No. 5,661,033; U.S. Pat. No. 5,328,688 each incorporated herein by reference) vector. In preferred embodiments, retroviral vectors are used to introduce the expression construct into HEK293 cells.

Screening for Modulators of Sodium Channel Protein

The present invention also contemplates the use of chimp NaV1.8 of the present invention and active fragments thereof in the screening of compounds that modulate (increase or decrease) activity of sodium channels. Such modulators and particularly sodium channel blockers will be useful as therapeutic agents. Assays for the identification of these agents may make use of splice variants of the invention in a variety of different formats and may depend on the kind of "activity" for which the screen is being conducted.

a. Assay Formats.

The present invention provides methods of screening for modulators of chimp NaV1.8's sodium channel activity in vitro and in vivo in the presence and absence of the candidate substance and comparing such results. It is contemplated that this screening technique will prove useful in the general identification of compounds of therapeutic value against e.g., pain, inflammation, and other diseases or disorders associated with sodium channel activity. In preferred embodiments, it will be desirable to identify inhibitors of sodium channel activity. However, in other embodiments, stimulators of such activity also may be desirable.

In the screening embodiments, the present invention is directed to a method for determining the ability of a candidate substance to alter the sodium channel activity of cells that express chimp NaV1.8 as described herein. Alternatively, the present application teaches the use of models for determining the in vivo effects of such compounds. The cells or animals also may then be contacted with additional sodium channel blockers in combination with a putative modulator of sodium channel function in order to determine whether the effect of such sodium channel blockers is increased or decreased as a result of the presence of the candidate substance.

An alteration in sodium channel activity, expression or processing in the presence of the candidate substance will indicate that the candidate substance is a modulator of the activity.

While the above method generally describes sodium channel activity, it should be understood that candidate substance may be an agent that alters the expression of sodium channel protein, thereby increasing or decreasing the amount of NaV1.8 protein present as opposed to the per unit activity of the protein.

To identify a candidate substance as being capable of inhibiting protein activity, one would measure or determine the protein activity in the absence of the added candidate substance. One would then add the candidate inhibitory substance to the cell and determine the activity of protein in the presence of the candidate inhibitory substance. A candidate substance which is inhibitory would decrease the sodium channel activity. Exemplary such assays are described below.

b. Candidate Substances.

As used herein the term "candidate substance" refers to any molecule that is capable of modulating sodium channel chimp NaV1.8 activity or expression. The candidate substance may be a protein or fragment thereof, a small molecule inhibitor, or even a nucleic acid molecule. It may prove to be the case that the most useful pharmacological compounds for identification through application of the screening assay will be compounds that are structurally related to other known modulators of sodium channels. The active compounds may include fragments or parts of naturally-occurring compounds or may be only found as active combinations of known compounds which are otherwise inactive. However, prior to testing of such compounds in humans or animal models, it will be necessary to test a variety of candidates to determine which have potential.

Accordingly, the active compounds may include fragments or parts of naturally-occurring compounds or may be found as active combinations of known compounds which are otherwise inactive. Accordingly, the present invention provides screening assays to identify agents which inhibit or otherwise treat a disorder or associated with sodium channel activity. It is proposed that compounds isolated from natural sources, such as animals, bacteria, fungi, plant sources, including leaves and bark, and marine samples may be assayed as candidates for the presence of potentially useful pharmaceutical agents.

It will be understood that the pharmaceutical agents to be screened could also be derived or synthesized from chemical compositions or man-made compounds. Thus, it is understood that the candidate substance identified by the present invention may be polypeptide, polynucleotide, small molecule inhibitors or any other inorganic or organic chemical compounds that may be designed through rational drug design starting from known agents that are used in the intervention of pain, inflammation or other diseases/disorders associated with sodium channel activity.

The candidate screening assays are relatively straightforward to set up and perform to one skilled in the art. Thus, in assaying for a candidate substance, after obtaining a cell expressing functional chimp NaV1.8 of the invention, one will admix a candidate substance with the cell, under conditions which would allow measurable sodium channel activity to occur. Exemplary sodium channel assays are provided below. In this fashion, one can measure the ability of the candidate substance to stimulate the activity of the cell in the absence of the candidate substance. Likewise, in assays for inhibitors after obtaining a cell expressing functional chimp NaV1.8, the candidate substance is admixed with the cell. In this fashion the ability of the candidate inhibitory substance to reduce, abolish, or otherwise diminish a biological effect mediated by chimp NaV1.8(s) from said cell may be detected.

"Effective amounts" in certain circumstances are those amounts effective to reproducibly alter sodium channel associated activity of the cell or animal in comparison to the normal levels of such an event. Compounds that achieve significant appropriate changes in such activity will be used.

Significant changes in a given sodium channel activity or in vivo function (discussed below) of at least about 30%-40%, and most preferably, by changes of at least about 50%, with higher values of course being possible. The active compounds of the present invention also may be used for the generation of antibodies which may then be used in analytical and preparatory techniques for detecting and quantifying further such inhibitors.

Proteins are often used in high throughput screening (HTS) assays known in the art, including melanophore assays to investigate receptor ligand interactions, yeast based assay systems and mammalian cell expression systems. For a review see Jayawickreme and Kost, Curr. Opin. Biotechnol., 8: 629-634 (1997). Automated and miniaturized HTS assays are also contemplated as described for example in Houston and Banks Curr. Opin. Biotechnol., 8: 734-740 (1997).

There are a number of different libraries used for the identification of small molecule modulators including chemical libraries, natural product libraries and combinatorial libraries comprised or random or designed peptides, oligonucleotides or organic molecules. Chemical libraries consist of structural analogs of known compounds or compounds that are identified as hits or leads via natural product screening or from screening against a potential therapeutic target. Natural product libraries are collections of products from microorganisms, animals, plants, insects or marine organisms which are used to create mixtures of screening by, e.g., fermentation and extractions of broths from soil, plant or marine organisms. Natural product libraries include polypeptides, non-ribosomal peptides and non-naturally occurring variants thereof. For a review see Science, 282:63-68 (1998). Combinatorial libraries are composed of large numbers of peptides oligonucleotides or organic compounds as a mixture. They are relatively simple to prepare by traditional automated synthesis methods, PCR cloning or other synthetic methods. Of particular interest will be libraries that include peptide, protein, peptidomimetic, multiparallel synthetic collection, recombinatorial and polypeptide libraries. A review of combinatorial libraries and libraries created therefrom, see Myers Curr. Opin. Biotechnol., 8: 701-707 (1997). A candidate modulator identified by the use of various libraries described may then be optimized to modulate activity of chimp NaV1.8 through, for example, rational drug design.

It will, of course, be understood that all the screening methods of the present invention are useful in themselves notwithstanding the fact that effective candidates may not be found. The invention provides methods for screening for such candidates, not solely methods of finding them.

c. In Vitro Assays.

Those of skill in the art are aware of numerous variations of in vitro methods for measuring sodium channel activity. Cells that express the given sodium channel being tested e.g., a neuronal cell line (from any eukaroyotic, preferably mammalian source) that has been transformed or transfected with a nucleic acid that encodes a protein of SEQ ID NO: 2 or alternatively, a primary mammalian cell culture e.g., neurons that naturally express a protein of SEQ ID NO: 2 are obtained. Primary cells from e.g., a rat source can be prepared as taught in Gallo et al., 1990 (J. Neurochem: 54, 1619-25 or Example 155 of U.S. Pat. No. 6,756,400). The cells are plated in an appropriate support e.g., in 96-well poly-D-lysine-coated black wall-clear bottom culture plates at a suitable concentration (e.g., $1-2\times 10^5$ cells/well of a 96-well plate). The cells are maintained at 37° C. in an atmosphere containing 5% $CO_2$.

To measure sodium channel activity, veratridine-evoked increases in intracellular $Ca^{2+}$ ($[Ca^{2+}]i$) in fluo-4/AM loaded cerebellar granule neurons may be monitored, in real-time, using a Fluorescent Imaging Plate Reader (FLIPR™, Molecular Devices, Sunnyvale, Calif.). The cells are incubated with 4 mM fluo-4/AM in HBSS buffer containing 2.5 mM probenecid and 0.04% pluronic acid for 45 min at 37° C. The cells are then washed three times with HBSS containing 2.5 mM probenecid (FLIPR™ buffer). The plates are transferred to the FLIPR™ and the cells incubated for 5 min in FLIPR™ buffer, in the absence (control) or presence of the test compound, prior to addition of veratridine (40 µM). Cell fluorescence ($\lambda_{Ex}$=488 nm; $\lambda_{Em}$=510 nm) is monitored both before and after the addition of veratridine. Peak fluorescence intensity, after veratridine addition, is determined using the FLIPR™ software. Curve fitting and parameter estimation ($pIC_{50}$) were performed using GraphPad. Stock solutions (10 mM) of compounds were made in 100% DMSO.

As an alternative to FLIPR™, the VIPR™ (Aurora Biosciences Corporation) assay may be used. In such an alternative assay, HEK293 cells expressing chimp NaV1.8 channels are cultured on 96- or 384-well plates (Costar tissue culture treated 96-well flat bottom plates, Corning). To prevent detachment of cells during plate washing, these plates are pre-coated with 0.5% Growth Factor Reduced matrigel matrix in DMEM for 1 hour at room temperature before use for cell culture. About 40,000 cells are seeded to each well and incubated at 38° C. for 24 hours before assay. Assay is performed at room temperature. The cell plates are first washed three times with bath solution using automatic plate washer (ELx405, Biotek), leaving a residual volume of 50 µL/well. Subsequently, cells are incubated with mixed dye solution for 30 min in the dark at room temperature. The mixed dye solution is prepared with External solution and consists of 10 µM CC2-DMPE (chlorocoumarin-2-dimyristoyl phosphatidylethanolamine), 2.4 µM $DISBAC_6(3)$ (bis-(1,3-dihexyl-thiobarbituric acid) trimethine oxonol), 0.5% β-cyclodextrin, 20 µg/ml pluronic F-127 and ESS Acid Yellow 17 (ESS AY-17). Thereafter, the cells are washed three times again with bath solution and then incubated with bath solution containing 0.5 mM ESS AY-17 and test compounds at desired concentrations for 10 min before assay.

A VIPR is equipped with instrumentation capable of electrical stimulation of cells expressing chimp NaV1.8 (see U.S. Pat. No. 6,686,193). This allows manipulation of the membrane potential and modulates the chimp NaV1.8 conductance. Sodium channels have brief (~1-3 ms) open times, so a train of electric field pulses is used to cycle the channel through open and closed conformations repeatedly. Membrane potential changes caused by the sodium influx through the channels is converted to optical signals using the Aurora FRET voltage sensitive dyes, described above. Cells stained with CC2-DMPE and $DiSBAC_6(3)$ are excited at 405 nm. The instrument is able to continually monitor the fluorescent output at two wavelengths for FRET measurement. Fluorescence responses are obtained at two wavelengths, 460 nm for CC2-DMPE and 580 nm for $DiSBAC_6(3)$.

The IC50 values of the tested compounds may be determined using an assay such as the one set forth above or any other conventional assay that measures sodium channel activity. Compounds that are effective in such in vitro assays may be tested in subsequent in vivo assays as described below.

Such assays are highly amenable to automation and high throughput. High throughput screening of compounds is described in WO 84/03564.

Of particular interest in this format will be the screening of a variety of different chimp NaV1.8. These mutants, including additional deletion, truncation, insertion and substitution mutants, will help identify which domains are involved with the functional channel forming activity of the chimp NaV1.8 of the invention. Once this region(s) or amino acids particularly important to the channel forming properties of the chimp NaV1.8 that have the sequences of SEQ ID NO: 2 have been determined, it will be possible to identify which of these mutants have altered structure but retain some or all of the biological functions of the sodium channel.

For example, each of the amino acids may be separately switched to an alanine residue and an "alanine scan" performed to determine which of the residues is important in determining activity. In additional embodiments, it is contemplated that each of the amino acids in this domain may be separately switched to another amino acid that is a conservative substitution of the native residue depending on the hyrophobicity, hydrophilicity or other characteristics of the amino acid at a given residue. To this effect, the SIFT (Sorting Intolerant From Tolerant) program is an exemplary program that allows the skilled artisan to predict whether an amino acid substitution affects protein function and can distinguish between functionally neutral and deleterious amino acid changes in mutagenesis studies (Ng and Henikoff, Nucleic Acid. Res., 31(13): 3812-3814 (2003))

Purified chimp NaV1.8 or its binding agent can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link the chimp NaV1.8 active region to a solid phase.

Other forms of in vitro assays include those in which functional readouts are taken. For example cells in which a chimp NaV1.8 is expressed can be treated with a candidate substance. In such assays, the substance would be formulated appropriately, given its biochemical nature, and contacted with the cell. Depending on the assay, culture may be required. The cell may then be examined by virtue of a number of different physiologic assays, as discussed above. Alternatively, molecular analysis may be performed in which the cells characteristics are examined. This may involve assays such as those for protein expression, enzyme function, substrate utilization, mRNA expression (including differential display of whole cell or polyA RNA) and others. Yet another assay format that can be contemplated is the use of a binding assay with a suitably labeled ligand that binds to the expressed protein. An example of such an assay would be the displacement by a small molecule of a radiolabeled or fluorescently labeled ligand from the expressed chimp NaV1.8. Such an assay can be used to identify potential small molecule modulators of the channel especially if the site where the labeled ligand binds is known to affect channel activity or regulation.

d. In Vivo Assays.

The present invention also encompasses the use of various animal models. In exemplary embodiments, the in vivo assays are set up to identify agents that modulate the sodium channel and are effective as analgesic or anti-inflammatory agents. The ability of an agent or a combination of agents to treat pain can be determined using known pharmacological models (for example see Kim, S. H. and Chung, J. M., Pain, 50: 355-363 (1992), or using models that are similar to known models. For example, to test baseline pain responses, tests such as mechanical withdrawal frequencies by application of different forces of calibrated von Frey monofilaments (mN: 0.24, 1.47, 4.33, 8.01, 23.69, 40.31) (Stoelting, Wood Dale, Ill.) to the plantar hind paw surface, or thermal withdrawal latencies after the application of radiant heat to the plantar hind paw surface may be used (Mansikka et al., Exp Neurol, 162: 343-349 (2000); Tao et al., Neuroscience, 98: 201-206 (2000)). Mechanical withdrawal frequencies are assessed by applying calibrated von Frey monofilaments 0.24 and 4.33 mN to the plantar hind paw surface (Fairbanks et al., Proc Natl Acad Sci USA, 97: 10584-10589 (2000); Mansikka et al., Exp Neurol, 162: 343-349 (2000)).

Male Sprague-Dawley rats are pre-screened to determine their baseline 50% withdrawal threshold using a set of von Frey filaments. The 50% withdrawal threshold for mechanical stimulation to the hind paw is determined by the up-down method described by Dixon W. J., Ann. Rev. Pharmacol. Toxicol., 20: 441-462 (1980). Briefly, 8 von Frey filaments with approximately equal logarithmic incremental (0.22) bending forces are chosen (von Frey numbers: 3.65, 3.87, 4.10, 4.31, 4.52, 4.74, 4.92, and 5.16; equivalent to: 0.45, 0.74, 1.26, 2.04, 3.31, 5.50, 8.32, and 14.45 g). A von Frey filament is applied perpendicularly to the plantar surface with sufficient force to bend it slightly and held for 3-5 seconds. An abrupt withdrawal of the foot during stimulation or immediately after the removal of stimulus is considered a positive response.

Whenever there is a positive or negative response, the next weaker or stronger filament is applied, respectively. The test is continued until six stimuli after the first change in response has been obtained. The pattern of positive and negative responses may then be converted into a 50% threshold value using various formulae known to those of skill in the art. One such formula is: 50% threshold=$10^{(X+kd)}/10^4$, where X=the value of the final von Frey filament used (in log units), k=the tabular value for the pattern of positive/negative responses [obtained from Dixon, *Annu Rev Pharmacol Toxicol* 20:441-462], and d=the mean difference between stimuli in log units (0.22). In the cases where continuous positive or negative responses are observed all the way out to the end of the stimulus spectrum, values of 0.3 g or 15.0 g are assigned, respectively. For $ED_{50}$ calculations, a linear regression is determined for responses one either side of the 50% reversal and then an approximation is determined based upon the value which intersects the 50% point.

Other in vivo methods of testing pain include hotplate analgesia meter determinations. Such hotplate methods evaluate the reaction time of mice (or rats) dropped onto a heated surface and confronted with a heat stimulus applied to their plantar surface. When an analgesic agent is administered to the animals, their reaction time is markedly increased. Such methods may be assessed using e.g., the SDI Hotplate Analgesia Meter (San Diego Instruments, San Diego, Calif., USA).

Treatment of animals with test compounds will involve the administration of the compound, in an appropriate form, to the animal. Administration will be by any route that can be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood, cerebrospinal fluid (CSF) or lymph supply and intratumoral injection.

Determining the effectiveness of a compound in vivo may involve a variety of different criteria. Such criteria include, but are not limited to, survival, reduction of tumor burden or mass, inhibition or prevention of inflammatory response, increased activity level, improvement in immune effector function and improved food intake.

Therapeutic Methods and Pharmaceutical Compositions

The present invention deals with the treatment of diseases that result from the increased activity (or expression) of sodium channel proteins. Compositions that inhibit the expression or overexpression of chimp NaV1.8 or block its sodium channel activity will be useful in treating or preventing a disease or condition associated with sodium channel activity.

The phrase "disease or condition associated with sodium channel activity" includes all disease states and/or conditions that are acknowledged now, or that are found in the future, to be associated with the activity of sodium channels. Such disease states include, but are not limited to, pathophysiological disorders, including hypertension, cardiac arrhythmogenesis, angina, insulin-dependent diabetes, non-insulin dependent diabetes mellitus, diabetic neuropathy, seizures, tachycardia, ischemic heart disease, cardiac failure, myocardial infarction, transplant rejection, autoimmune disease, sickle cell anemia, muscular dystrophy, gastrointestinal disease, mental disorder, sleep disorder, anxiety disorder, eating disorder, neurosis, alcoholism, inflammation, multiple sclerosis, cerebrovascular ischemia, CNS diseases, epilepsy, stroke, Parkinson's disease, asthma, incontinence, urinary dysfunction, micturition disorder, irritable bowel syndrome, restenosis, subarachnoid hemorrhage, Alzheimer's disease, drug dependence/addiction, schizophrenia, Huntington's chorea, tension-type headache, trigeminal neuralgia, cluster headache, migraine (acute and prophylaxis), inflammatory pain, neuropathic pain and depression.

Nucleic acid sequences, antisense molecules, PNAs, purified protein, antibodies, antagonists or inhibitors directed against chimp NaV1.8 can all be used as pharmaceutical compositions. Delivery of these molecules for therapeutic purposes is further described below. The most appropriate therapy depends on the patient, the specific diagnosis, and the physician who is treating and monitoring the patient's condition.

Where clinical applications are contemplated, it will be necessary to prepare the small molecules, analgesic compounds, viral expression vectors, antibodies, peptides, nucleic acids and other compositions identified by the present invention as pharmaceutical compositions, i.e., in a form appropriate for in vivo applications. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the compositions of the present invention, its use in therapeutic compositions is contemplated. Supplementary active ingredients also can be incorporated into the compositions.

The active compositions of the present invention include classic pharmaceutical preparations. Administration of these compositions according to the present invention will be via any common route so long as the target tissue is available via that route. The pharmaceutical compositions may be introduced into the subject by any conventional method, e.g., by intravenous, intradermal, intramuscular, intramammary, intraperitoneal, intrathecal, intraocular, retrobulbar, intrapulmonary (e.g., term release); by oral, sublingual, nasal, anal, vaginal, or transdermal delivery, or by surgical implantation at a particular site, e.g., embedded under the splenic capsule, brain, or in the cornea. The treatment may consist of a single dose or a plurality of doses over a period of time. A "subject" or "individual" as used herein, is a vertebrate, preferably a mammal, more preferably a human. Mammals include research, farm and sport animals, and pets.

The active compounds may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

A typical composition for intramuscular or intrathecal administration will consist of a suspension or solution of active ingredient in an oil, for example arachis oil or sesame oil. A typical composition for intravenous or intrathecal administration will consist of a sterile isotonic aqueous solution containing, for example active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol; a chelating agent, for example, ethylenediamine tetracetic acid; a solubilizing agent, for example, a cyclodextrin; and an antioxidant, for example, sodium metabisulphite, may be included in the formulation. Alternatively, the solution can be freeze dried and then reconstituted with a suitable solvent just prior to administration.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

In the clinical setting a "therapeutically effective amount" is an amount sufficient to effect beneficial or desired clinical results. An effective amount can be administered in one or more doses. The term "therapeutically effective amount" refers to an amount sufficient to effect treatment when administered to a patient in need of treatment. The term "treatment" as used herein refers to the treatment of a disease or medical condition in a patient, such as a mammal (particularly a human) which includes: preventing the disease or medical condition from occurring, i.e., prophylactic treatment of a patient; ameliorating the disease or medical condition, i.e., eliminating or causing regression of the disease or medical condition in a patient; suppressing the disease or medical condition, i.e., slowing or arresting the development of the disease or medical condition in a patient; or alleviating the symptoms of the disease or medical condition in a patient. Thus, in terms of treatment, a "therapeutically effective amount" of the given therapeutic agent is an amount sufficient to palliate, ameliorate, stabilize, reverse, slow or delay the progression of a disease or condition associated with sodium channel activity or otherwise reduce the pathological consequences of such a disease or condition. The effective amount is generally determined by the physician on a case-by-case basis and is within the skill of one in the art. Several factors are typically taken into account when determining, an appropriate dosage. These factors include age, sex and weight of the patient, the condition being treated, the severity of the condition and the form of the antibody being administered.

The therapeutic compositions can also comprise one or more additional agents effective in the treatment of a disease or disorder associated with sodium channel activity. Other compositions which inhibit the expression, activity or function of chimp NaV1.8 (e.g., antagonists) also are contemplated for use in such treatment methods. Thus, combination therapy for the treatment of a disease or disorder associated with sodium channel activity is specifically contemplated. In the context of the present invention, it is contemplated that chimp NaV1.8 inhibition therapy could be used similarly in conjunction with other analgesic agents or sodium channel blocker that are used in the treatment of such disorders.

To achieve the appropriate therapeutic outcome using the methods and compositions of the present invention, one would generally administer a first therapeutic agent that is a chimp NaV1.8 inhibitor or blocker as discussed herein and at least one other therapeutic agent (second therapeutic agent). These compositions would be provided in a combined amount effective to produce the desired therapeutic outcome. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second therapeutic agent.

Alternatively, the first therapeutic agent may precede or follow the other agent treatment by intervals ranging from minutes to weeks. In embodiments where the second therapeutic agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Local delivery of the first therapeutic agent (i.e., the inhibitor, stimulator or other agent that decreases or increases the amount or activity of chimp NaV1.8 in the individual) to patients may be a very efficient method for delivering a therapeutically effective gene to counteract a clinical disease. Similarly, the second therapeutic agent may be directed to a particular, affected region of the subject's body. Alternatively, systemic delivery of the first and/or second therapeutic agent may be appropriate in certain circumstances.

The active compound(s) is effective over a wide dosage range and is generally administered in a therapeutically effective amount. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

According to the invention, a compound can be administered in a single daily dose or in multiple doses per day. The treatment regimen may require administration over extended periods of time, for example, for several days or for from one to six weeks.

"Unit dose" is defined as a discrete amount of a therapeutic composition dispersed in a suitable carrier. Parenteral administration may be carried out with an initial bolus followed by continuous infusion to maintain therapeutic circulating levels of drug product. Those of ordinary skill in the art will readily optimize effective dosages and administration regimens as determined by good medical practice and the clinical condition of the individual patient. Suitable doses of sodium channel blockers are in the general range of from 0.01-100 mg/kg/day, preferably 0.1-50 mg/kg/day. For an average 70 kg human, this would amount to 0.7 mg to 7 g per day, or preferably 7 mg to 3.5 g per day. In general, an effective amount of a compound of this invention is a dose between about 0.5 and about 100 mg/kg. A preferred dose is from about 1 to about 60 mg/kg of active compound. A typical daily dose for an adult human is from about 50 mg to about 5 g.

The frequency of dosing will depend on the pharmacokinetic parameters of the agents and the routes of administration. The optimal pharmaceutical formulation will be determined by one of skill in the art depending on the route of administration and the desired dosage. See for example Remington's Pharmaceutical Sciences, 18th Ed. (1990), Mack Publ. Co, Easton Pa. 18042, pp 1435-1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

Appropriate dosages may be ascertained through the use of established assays for determining blood levels in conjunction with relevant dose response data. The final dosage regimen will be determined by the attending physician, considering factors which modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

In a preferred embodiment, the present invention is directed at treatment of human disorder, disease or condition associated with sodium channel activity, or may be alleviated by administering a sodium channel blocker or inhibitor. A variety of different routes of administration are contemplated. For example, a classic and typical therapy will involve direct, injection of a discrete area.

Further Uses of Compositions of the Invention

In certain embodiments of the invention, methods of diagnosing a disorder in which human NaV1.8 is overexpressed or aberrantly expressed are contemplated. Such diagnostic methods of the present invention are achieved through the detection of the human NaV1.8 or a fragment thereof that is expressed in abundance as compared to normal expression. Such abnormal expression may be detected using chimp NaV1.8 nucleic acid molecules that hybridize to human NaV1.8 nucleic acid molecules, or antibodies to chimp NaV1.8 that cross-react with human NaV1.8 in any of a number of formats commonly used by those of skill in the art for such detection.

It is further contemplated that certain diseases or disorders associated with overexpression of human NaV1.8 may be treated using chimp Nav1.8 nucleic acid molecules (e.g., antisense, siRNA) and/or antibodies according to the invention.

In another aspect, the present invention contemplates that an antibody that is immunoreactive with any sodium channel alpha subunit may be immunoreactive with the protein molecule of the present invention. Indeed, antibodies may be generated using the protein of SEQ ID NO: 2. Such antibodies include, but are not limited to, polyclonal, monoclonal, chimeric, single chain, Fab fragments and fragments produced by a Fab expression library, bifunctional/bispecific antibodies, humanized antibodies, CDR grafted antibodies, human antibodies and antibodies which include portions of CDR sequences specific for sodium channel protein of the present invention. Means for preparing and characterizing antibodies are well known in the art (see, e.g., Harlow and Lane, ANTIBODIES: A LABORATORY MANUAL, Cold Spring Harbor Laboratory, Cold Spring Harbor, N.Y. (1988)). Antibodies specifically immunoreactive to the chimp NaV1.8 that comprises a sequence of SEQ ID NO: 2 are particularly preferred.

It is proposed that antibodies specific for sodium channels will be useful in standard immunochemical procedures, such as ELISA and Western blot methods and in immunohistochemical procedures such as tissue staining to determine the distribution of sodium channels.

EXAMPLES

The following example is included to demonstrate preferred embodiments of the invention. It should be appreciated by those of skill in the art that the techniques disclosed in the example which follows represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A. Cloning of Chimp NaV1.8

The present example teaches the construction of chimp NaV1.8 cDNA clones. Chimp (*Pan troglodytes*) Dorsal Root Ganglion (DRG) was obtained from the Southwest National Primate Research Center by Dr. Ada Silos-Santiago (Vertex Pharmaceuticals). The tissue was disrupted in liquid nitrogen using a mortar and pestle and subsequently homogenized using a QIAshredder homogenizer. Total RNA was extracted using RNAeasy mini kit (QIAGEN). First strand cDNA synthesis was carried out using the Thermoscript RT-PCR System (Invitrogen). In addition to the kit components we used 150 ng of total RNA and 2.5 uM OligoDT primers in a total volume of 20 ul. The reaction was carried out at 50° C. for one hour, 60° C. for one hour and terminated at 80° C. for 15 minutes after which the RNA template was removed using RNaseH.

Human Nav1.8 (genbank accession #NM_006514) nucleotide sequence was used to design oligonucleotide primers in order to facilitate cloning of chimp NaV1.8 cDNA. First strand cDNA from the transcription reaction was used for PCR to obtain two fragments of NaV1.8 cDNA, termed fragment I (primers F1-22s and F1-19a) and fragment II (primers F2-21s and F2-24a). Fragment I (1-3423 bp) and fragment II (3319-5871 bp) overlap at a unique NsiI restriction site. The PfuUltra polymerase (Stratagene) was used for all PCR reactions in order to minimize the error rate during amplification. The cycling parameters included an initial denaturation step at 95° C. for 2 min followed by 10 cycles of 1 min at 95° C., 1 min at 57° C., 4 min at 72° C. and another 20 cycles of 1 min at 95° C., 1 min at 60° C., 4 min at 72° C. and a final extension at 72° C. for 10 min. Reaction samples were run on 1% agarose gels and the expected molecular weight band sizes were isolated (frag 1=3.3 kb and frag 2=2.5 kb). The two fragments were ligated into the PCR Blunt II TOPO vector (Invitrogen) and individual miniprep samples were sequenced using primers directed to the inserts.

The sequences were aligned with the human NaV1.8 sequence using VectorNTI Contig Express (Invitrogen) and the best sample for each fragment was selected. Using PCR conditions described above, a Kozak consensus sequence and an HpaI restriction site were introduced into the 5' end of Fragment 1 (primers F1-49s, F1-19a). A NotI restriction site was introduced at the 3' end of Fragment II (primers F2-21s, F2-48a). The integrity of the fragments was confirmed by sequencing. The final assembly into a mammalian expression vector was carried out in two steps. Fragment II was inserted into the pCLBCX vector and then Fragment II was inserted 3' of Fragment I to generate the full-length chimp NaV1.8 gene. The full-length chimp NaV1.8 gene was sequenced and the integrity of the construct was confirmed.

Table of Oligonucleotide Primers:

| | | |
|---|---|---|
| F1-49s | NNNNGTTAACTTCGCCACCATGGAATTCCCCATTGGA<br>TCCCTCGAAAC<br>(SEQ ID NO: 3) | |
| F1-22s | ATGGAATTCCCCATTGGATCCC<br>(SEQ ID NO: 4) | |
| F1-19a | CACCTGCCAGCCCACATCC<br>(SEQ ID NO: 5) | |
| F2-48a | NNNNGCGGCCGCCTCACTAGGGCCCAGGGGCAATCAG<br>CTCCATACTG<br>(SEQ ID NO: 6) | |
| F2-24a | CTAGGGCCCAGGGGCAATCAGCTC<br>(SEQ ID NO: 7) | |
| F2-21s | GACCTGGAAGAACCAGATGAC<br>(SEQ ID NO: 8) | |

B. Alignment of Human and Chimp NaV1.8

Sequencing and alignment of human and chimp NaV1.8 cDNA sequences showed 39 differences at the nucleotide level and some of these differences translated to a change in the amino acid sequence. The differences at the amino acid level are as follows:

Amino acid differences between human and chimp NaV1.8 sequence:
V138I
T368A
P571L
S639A
S935P
I962V
P1074S
L1092P
L1128V
M1527L All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references cited herein throughout, to the extent that they provide exemplary procedural or other details supplementary to those set forth herein, are all specifically incorporated herein by reference.

What is claimed is:

1. An isolated recombinant nucleic acid encoding a chimp sodium channel NaV1.8 polypeptide, wherein said polypeptide comprises:
   (a) a polypeptide sequence of SEQ ID NO: 2, or
   (b) a polypeptide encoded by a nucleic acid having the sequence of SEQ ID NO: 1 or degenerates thereof, wherein the degenerates encode the polypeptide of SEQ ID NO: 2.

2. The isolated nucleic acid of claim 1, wherein said nucleic acid is derived from genomic DNA.

3. The isolated nucleic acid of claim 1, wherein said nucleic acid is derived from cDNA.

4. An expression construct comprising an isolated nucleic acid encoding a protein having an amino acid sequence of SEQ ID NO: 2, and a promoter operably linked to said nucleic acid.

5. The expression construct of claim 4, wherein said nucleic acid comprises a protein coding sequence of SEQ ID NO: 1.

6. The expression construct of claim 4, wherein said expression construct is an expression construct selected from the group consisting of an adenoassociated viral construct, an adenoviral construct, a herpes viral expression construct, a vaccinia viral expression construct, a retroviral expression construct, a lentiviral expression construct and a naked DNA expression construct.

7. A recombinant host cell stably transformed or transfected with a nucleic acid of claim 1, in a manner allowing the expression in said host cell of a polypeptide of SEQ ID NO: 2.

8. A method of producing a chimp sodium channel NaV1.8 polypeptide comprising the steps of:
   i) preparing an expression construct comprising a nucleic acid of SEQ ID NO: 1 and degenerates thereof operably linked to a promoter, wherein the degenerates encode the polypeptide of SEQ ID NO: 2;
   ii) transforming or transfecting a host cell with said expression construct in a manner effective to allow the expression of a polypeptide having an amino acid sequence of SEQ ID NO: 2, or the mature protein portion thereof in said host cell; and
   iii) culturing said transformed or transfected cell under conditions to allow the production of said polypeptide by said transformed or transfected host cell.

9. A diagnostic kit for detecting a nucleic acid that encodes a chimp sodium channel NaV1.8 polypeptide, the polypeptide being encoded by a nucleic acid having the sequence of SEQ ID NO:1 and degenerates thereof, comprising an isolated nucleic acid probe complementary to the sequence selected from the group consisting of SEQ ID NO: 1 and degenerates thereof, and means for containing said nucleic acid, wherein the degenerates encode the polypeptide of SEQ ID NO: 2.

10. A method of identifying a modulator of a chimp sodium channel NaV1.8 polypeptide expression or activity identified by a method comprising the steps of:
   i) contacting a cell that expresses a nucleic acid of SEQ ID NO: 1 or degenerates thereof with the candidate modulator substance, wherein the degenerates encode the polypeptide of SEQ ID NO: 2;
   ii) monitoring the expression or ion channel activity of a protein of SEQ ID NO: 2; and
   iii) comparing the expression or ion channel activity of a protein of SEQ ID NO: 2 in the presence and absence of said candidate substance;
   wherein an alteration in the expression or ion channel activity of a protein of SEQ ID NO: 2 indicates that the substance is a modulator of chimp sodium channel NaV1.8 polypeptide expression or activity.

11. A method of identifying a test compound that binds to a chimp sodium channel NaV1.8 comprising:
   i) providing a cell that expresses a chimp sodium channel NaV1.8 polypeptide having a sequence of SEQ ID NO: 2;
   ii) contacting the host cell with said test compound and determining the binding of said test compound to the sodium channel; and
   iii) comparing the binding of the test compound to the host cell determined in step (b) to the binding of said test compound with a cell that does not express a sodium channel.

12. An assay method for identifying a test compound that modulates the activity of a chimp sodium channel NaV1.8 comprising:
   i) providing a host cell that expresses a chimp sodium channel NaV1.8 polypeptide having a sequence of SEQ ID NO: 2;
   (ii) contacting the host cell with a test compound under conditions that would activate sodium channel activity of said sodium channel in the absence of the test compound; and
   (iii) determining whether the host cell contacted with the test compound exhibits a modulation in activity of the sodium channel.

* * * * *

SEQUENCE LISTING

<160> NUMBER OF SEQ ID NOS: 8

<210> SEQ ID NO 1
<211> LENGTH: 5871
<212> TYPE: DNA
<213> ORGANISM: Pan troglodytes

<400> SEQUENCE: 1

```
atggaattcc ccattggatc cctcgaaact aacaacttcc gtcgctttac tccggagtca      60
ctggtggaga tagagaagca aattgctgcc aagcagggaa caaagaaagc cagagagaag     120 cataggagc agaaggacca agaagagaag cctcggcccc agctagactt gaaagcctgc      180
aaccagctgc ccaagttcta tggtgagctc ccagcagaac tgatcgggga gcccctggag     240
gatctagatc cgttctacag cacacaccgg acatttatgg tgctgaacaa agggaggact     300
atttcccggt ttagtgccac tcgggccctg tggctattca gtccttttcaa cctgatcaga     360 agaacggcca tcaaagtgtc tgtccactcg tggttcagtt tatttattac gatcactatt     420
ttggttaatt gtgtgtgcat gacccgaact gaccttccag agaaaattga atatgtcttc     480
actgtcattt acacctttga agccttgata aagatactgg caagaggatt ttgtctaaat     540
gagttcacgt acctgagaga tccttggaac tggctggatt ttagcgtcat tacccctgca     600
tatgttggca gcaatagac tctccgtggg atctcaggcc tgcggacatt cagagttctt     660
agagcattaa aaacagtttc tgtgatccca ggcctgaagg tcattgtggg ggccctgatt     720
cactcagtga agaaactggc tgatgtgacc atcctcacca tcttctgcct aagtgttttt     780
gccttggtgg ggctgcaact cttcaagggg aacctcaaaa ataaatgtgt caagaatgac     840
atggctgtca atgagacaac caactactca tctcacagaa aaccagatat ctacataaat     900
aagcgaggca cttctgaccc cttactgtgt ggcaatggat ctgactcagg ccactgccct     960
```

```
gatggttata tctgccttaa aacttcggac aacccggatt ttaactacac cagctttgat   1020
tcctttgctt gggctttcct ctcactgttc cgcctcatga cacaggattc ctgggaacgc   1080
ctctaccagc agaccctgag ggcttctggg aaaatctata tgatctttt tgtgctcgta   1140 atcttcctgg gatctttcta cctggtcaac ttgatcttgg ctgtagtcac catggcatat   1200
gaggagcaga accaggcaac cactgatgaa attgaagcaa aggagaagaa gttccaggag   1260
gccctcgaga tgctccggaa ggagcaggag gtgctagcag cactagggat tgacacaacc   1320
tctctccact cccacaatgg atcacctta acctccaaaa atgccagtga gagaaggcat   1380
agaataaagc caagagtgtc agagggctcc acagaagaca acaaatcacc ccgctctgat   1440
ccttacaacc agcgcaggat gtcttttcta ggcctcgcct ctggaaaacg ccgggctagt   1500
catggcagtg tattccattt ccggtcccct ggccgagata tctcactccc tgagggagtc   1560
acagatgatg gagtctttcc tggagaccac gaaagccatc ggggctctct gctgctgggt   1620
gggggtgctg gccagcaagg ccccctccct agaagccctc ttcctcaacc cagcaaccct   1680
gactccaggc atggaagaa tgaacaccaa ctgccaccca ctagtgagct tgcccctgga   1740
gctgtcgatg tctcggcatt cgatgcagga caaaagaaga cttcttgtc agcagaatac   1800 ttagatgaac ctttccgggc ccaaagggca atgagtgttg tcagtatcat aacctccgtc   1860
cttgaggaac tcgaggagtc tgaacagaag tgcccaccct gcttgaccag cttggctcag   1920
aagtatctga tctgggattg ctgccccatg tgggtgaagc tcaagacaat tctctttggg   1980
cttgtgacgg atccctttgc agagctcacc atcaccttgt gcatcgtggt gaacaccatc   2040
ttcatggcca tggagcacca tggcatgagc cctaccttcg aagccatgct ccagataggc   2100
aacattgtct ttaccatatt ttttactgcc gaaatggtct tcaaaatcat tgccttcgac   2160
ccatactatt atttccagaa gaagtggaat atctttgact gcatcatcgt cactgtgagt   2220
ctgctagagc tgggcgtggc caagaaggga agcctgtctg tgctgcggag cttccgcttg   2280
ctgcgcgtat tcaagctggc caaatcctgg cccaccttaa acacactcat caagatcatc   2340
ggaaactcag tggggcact ggggaacctc accatcatcc tggccatcat tgtcttttgtc   2400 tttgctctgg ttggcaagca gctcctaggg gaaaactacc gtaacaaccg aaaaaatatc   2460
tccgcgcccc atgaagattg gccccgctgg cacatgcacg acttcttcca ctctttcctc   2520
attgtcttcc gtatcctctg tggagagtgg attgagaaca tgtgggcctg catggaagtc   2580
ggccaaaaat ccatatgcct catccttttc ttgacggtga tggtgctagg gaacctggtg   2640
gtgcttaacc tgttcatcgc cctgctattg aactctttca gtgctgacaa cctcacagcc   2700
ccggaggacg atggggaggt gaacaacctg caggtggccc tggcacggat ccaggtcttt   2760
ggccatcgta ccaagcaggc tctttgcagc ttcttcagca ggccctgccc attccccag   2820 cccaaggcag agcctgagct ggtggtgaaa ctcccactct ccagctccaa ggctgagaac   2880
cacgttgctg ccaacactgc caggggagc tctggagggc tccaagctcc cagaggcccc   2940
agggatgagc acagtgactt catcgctaat ccgactgtgt gggtctctgt gcccattgct   3000
gagggcgaat ctgatcttga tgacttggag gatgatggtg gggaagatgc tcagagcttc   3060
cagcaggaag tgatccccaa aggacagcag gagcagctgc agcaagtcga gaggtgtggg   3120
gaccacctga cacccaggag cccaggcact ggaacatctt ctgaggacct ggctccatcc   3180
ctgggtgaga cgtggaaaga tgagtctgtt cctcaggcct ctgccgaggg agtggacgac   3240
acaagctcct ctgagggcag cacagtggac tgcccagatc ctgaggagat cctgaggaag   3300
atccctgagc tggcagatga cctggaagaa ccagatgact gcttcacaga aggatgcatt   3360
```

```
cgccactgtc cttgctgcaa agtggatacc accaagagtc catgggatgt gggctggcag    3420
gtgcgcaaga cttgctaccg tatcgtggag cacagctggt ttgagagctt catcatcttc    3480
atgatcctgc tcagcagtgg atctctggcc tttgaagact attacctgga ccagaagccc    3540
acggtgaaag ctttgctgga gtacactgac agggtcttca cctttatctt tgtgtttgag    3600
atgctgctta agtgggtggc ctatggcttc aaaaagtact tcaccaatgc ctggtgctgg    3660
ctggacttcc tcattgtgaa tatctcactg ataagtctca cagcgaagat tctggaatat    3720
tctgaagtgg ctcccatcaa agcccttcga acccttcgcg ctctgcggcc actgcgggct    3780 cttttctcgat ttgaaggcat gcgggtggtg gtggatgccc tggtgggcgc catcccatcc    3840
atcatgaatg tcctcctcgt ctgcctcatc ttctggctca tcttcagcat catgggcgtg    3900
aacctcttcg cagggaagtt ttggaggtgc atcaactata ccgatggaga gttttccctt    3960
gtacctttgt cgattgtgaa taacaagtct gactgcaaga ttcaaaactc caccggcagc    4020
ttcttctggg tcaatgtgaa agtcaacttt gataatgttg caatgggtta ccttgcactt    4080
ctgcaggtgg caacctttaa aggctggatg gacattatgt atgcagctgt tgattcccgg    4140
gaggttaaca tgcaacccaa gtgggaggac aacgtgtaca tgtatttgta ctttgtcatc    4200
ttcatcattt ttggaggctt cttcacactg aatctctttg ttggggtcat aattgacaac    4260
ttcaatcaac agaaaaaaaa gttaggggc caggacatct tcatgacaga ggagcagaag    4320
aagtactaca atgccatgaa gaagttgggc tccaagaagc ccagaagcc catcccacgg    4380 cccctgaaca agttccaggg ttttgtcttt gacatcgtga ccagacaagc ttttgacatc    4440
accatcatgg tcctcatctg cctcaacatg atcaccatga tggtggagac tgatgaccaa    4500
agtgaagaaa agacgaaaat tctgggcaaa atcaaccagt tctttgtggc cgtcttcaca    4560
ggcgaatgtg tcatgaagct gttcgctttg aggcagtact acttcacaaa tggctggaat    4620
gtgtttgact tcattgtggt ggttctctcc attgcgagcc tgattttttc tgcaattctt    4680
aagtcacttc aaagttactt ctcccccgacg ctcttcagag tcatccgcct ggcccgaatt    4740
ggccgcatcc tcagactgat ccgagcggcc aaggggatcc gcacactgct ctttgccctc    4800
atgatgtccc tgcctgccct cttcaacatc gggctgttgc tattccttgt catgttcatc    4860
tactccatct tcggtatgtc cagctttccc catgtgaggt gggaggctgg catcgacgac    4920
atgttcaact tccagacctt cgccaacagc atgctgtgcc tcttccagat caccacgtcg    4980
gccggctggg atggcctcct cagccccatc ctcaacactg gcccccccta ctgtgacccc    5040
aatctgccca acagcaatgg caccagaggg gactgtggga gcccagccgt aggcatcatc    5100
ttcttcacca cctacatcat catctccttc ctcatcgtgg tcaacatgta cattgcagtg    5160
attctggaga acttcaatgt ggccacggag gagagcaccg agccctgag tgaggacgac    5220 tttgacatgt tctatgagac ctgggagaag tttgacccag aggccactca gtttattacc    5280
ttttctgctc tctcggactt tgcagacact ctctctggtc ccctgagaat cccaaaaccc    5340
aatcgaaata tactgatcca gatggaccctg cctttggtcc ctggagataa gatccactgc    5400
ttggacatcc tttttgcttt caccaagaat gtcctaggag aatccgggga gttggattct    5460
ctgaaggcaa atatggagga gaagtttatg caactaatc tttcaaaatc atcctatgaa    5520
ccaatagcaa ccactctccg atggaagcaa gaagacattt cagccactgt cattcaaaag    5580
gcctatcgga gctatgtgct gcaccgctcc atggcactct ctaacacccc atgtgtgccc    5640
agagctgagg aggaggctgc atcactccca gatgaaggtt ttgttgcatt cacagcaaat    5700
gaaaattgtg tactcccaga caaatctgaa actgcatctg ccacatcatt cccaccgtcc    5760
```

```
tatgagagtg tcactagagg ccttagtgat agagtcaaca tgaggacatc tagctcaata    5820
caaaatgaag atgaagccac cagtatggag ctgattgccc ctgggcccta g             5871
```

<210> SEQ ID NO 2
<211> LENGTH: 1956
<212> TYPE: PRT
<213> ORGANISM: Pan troglodytes

<400> SEQUENCE: 2

```
Met Glu Phe Pro Ile Gly Ser Leu Glu Thr Asn Asn Phe Arg Arg Phe
1               5                   10                  15

Thr Pro Glu Ser Leu Val Glu Ile Glu Lys Gln Ile Ala Ala Lys Gln
            20                  25                  30

Gly Thr Lys Lys Ala Arg Glu Lys His Arg Glu Gln Lys Asp Gln Glu
        35                  40                  45

Glu Lys Pro Arg Pro Gln Leu Asp Leu Lys Ala Cys Asn Gln Leu Pro
    50                  55                  60

Lys Phe Tyr Gly Glu Leu Pro Ala Glu Leu Ile Gly Glu Pro Leu Glu
65                  70                  75                  80

Asp Leu Asp Pro Phe Tyr Ser Thr His Arg Thr Phe Met Val Leu Asn
                85                  90                  95

Lys Gly Arg Thr Ile Ser Arg Phe Ser Ala Thr Arg Ala Leu Trp Leu
            100                 105                 110

Phe Ser Pro Phe Asn Leu Ile Arg Arg Thr Ala Ile Lys Val Ser Val
        115                 120                 125

His Ser Trp Phe Ser Leu Phe Ile Thr Ile Thr Ile Leu Val Asn Cys
    130                 135                 140

Val Cys Met Thr Arg Thr Asp Leu Pro Glu Lys Ile Glu Tyr Val Phe
145                 150                 155                 160

Thr Val Ile Tyr Thr Phe Glu Ala Leu Ile Lys Ile Leu Ala Arg Gly
                165                 170                 175

Phe Cys Leu Asn Glu Phe Thr Tyr Leu Arg Asp Pro Trp Asn Trp Leu
            180                 185                 190

Asp Phe Ser Val Ile Thr Leu Ala Tyr Val Gly Thr Ala Ile Asp Leu
        195                 200                 205

Arg Gly Ile Ser Gly Leu Arg Thr Phe Arg Val Leu Arg Ala Leu Lys
    210                 215                 220

Thr Val Ser Val Ile Pro Gly Leu Lys Val Ile Val Gly Ala Leu Ile
225                 230                 235                 240

His Ser Val Lys Lys Leu Ala Asp Val Thr Ile Leu Thr Ile Phe Cys
                245                 250                 255

Leu Ser Val Phe Ala Leu Val Gly Leu Gln Leu Phe Lys Gly Asn Leu
            260                 265                 270

Lys Asn Lys Cys Val Lys Asn Asp Met Ala Val Asn Glu Thr Thr Asn
        275                 280                 285

Tyr Ser Ser His Arg Lys Pro Asp Ile Tyr Ile Asn Lys Arg Gly Thr
    290                 295                 300

Ser Asp Pro Leu Leu Cys Gly Asn Gly Ser Asp Ser Gly His Cys Pro
305                 310                 315                 320

Asp Gly Tyr Ile Cys Leu Lys Thr Ser Asp Asn Pro Asp Phe Asn Tyr
                325                 330                 335

Thr Ser Phe Asp Ser Phe Ala Trp Ala Phe Leu Ser Leu Phe Arg Leu
            340                 345                 350

Met Thr Gln Asp Ser Trp Glu Arg Leu Tyr Gln Gln Thr Leu Arg Ala
```

-continued

```
              355                 360                 365
Ser Gly Lys Ile Tyr Met Ile Phe Phe Val Leu Val Ile Phe Leu Gly
370                 375                 380

Ser Phe Tyr Leu Val Asn Leu Ile Leu Ala Val Val Thr Met Ala Tyr
385                 390                 395                 400

Glu Glu Gln Asn Gln Ala Thr Thr Asp Glu Ile Glu Ala Lys Glu Lys
                405                 410                 415

Lys Phe Gln Glu Ala Leu Glu Met Leu Arg Lys Glu Gln Glu Val Leu
                420                 425                 430

Ala Ala Leu Gly Ile Asp Thr Thr Ser Leu His Ser His Asn Gly Ser
            435                 440                 445

Pro Leu Thr Ser Lys Asn Ala Ser Glu Arg Arg His Arg Ile Lys Pro
    450                 455                 460

Arg Val Ser Glu Gly Ser Thr Glu Asp Asn Lys Ser Pro Arg Ser Asp
465                 470                 475                 480

Pro Tyr Asn Gln Arg Arg Met Ser Phe Leu Gly Leu Ala Ser Gly Lys
                485                 490                 495

Arg Arg Ala Ser His Gly Ser Val Phe His Phe Arg Ser Pro Gly Arg
                500                 505                 510

Asp Ile Ser Leu Pro Glu Gly Val Thr Asp Asp Gly Val Phe Pro Gly
            515                 520                 525

Asp His Glu Ser His Arg Gly Ser Leu Leu Gly Gly Gly Ala Gly
        530                 535                 540

Gln Gln Gly Pro Leu Pro Arg Ser Pro Leu Pro Gln Pro Ser Asn Pro
545                 550                 555                 560

Asp Ser Arg His Gly Glu Asp Glu His Gln Leu Pro Pro Thr Ser Glu
                565                 570                 575

Leu Ala Pro Gly Ala Val Asp Val Ser Ala Phe Asp Ala Gly Gln Lys
            580                 585                 590

Lys Thr Phe Leu Ser Ala Glu Tyr Leu Asp Glu Pro Phe Arg Ala Gln
        595                 600                 605

Arg Ala Met Ser Val Val Ser Ile Ile Thr Ser Val Leu Glu Glu Leu
    610                 615                 620

Glu Glu Ser Glu Gln Lys Cys Pro Pro Cys Leu Thr Ser Leu Ala Gln
625                 630                 635                 640

Lys Tyr Leu Ile Trp Asp Cys Cys Pro Met Trp Val Lys Leu Lys Thr
                645                 650                 655

Ile Leu Phe Gly Leu Val Thr Asp Pro Phe Ala Glu Leu Thr Ile Thr
                660                 665                 670

Leu Cys Ile Val Val Asn Thr Ile Phe Met Ala Met Glu His His Gly
            675                 680                 685

Met Ser Pro Thr Phe Glu Ala Met Leu Gln Ile Gly Asn Ile Val Phe
    690                 695                 700

Thr Ile Phe Phe Thr Ala Glu Met Val Phe Lys Ile Ile Ala Phe Asp
705                 710                 715                 720

Pro Tyr Tyr Tyr Phe Gln Lys Lys Trp Asn Ile Phe Asp Cys Ile Ile
                725                 730                 735

Val Thr Val Ser Leu Leu Glu Leu Gly Val Ala Lys Lys Gly Ser Leu
            740                 745                 750

Ser Val Leu Arg Ser Phe Arg Leu Leu Arg Val Phe Lys Leu Ala Lys
        755                 760                 765

Ser Trp Pro Thr Leu Asn Thr Leu Ile Lys Ile Ile Gly Asn Ser Val
    770                 775                 780
```

-continued

Gly Ala Leu Gly Asn Leu Thr Ile Ile Leu Ala Ile Val Phe Val
785                 790                 795                 800

Phe Ala Leu Val Gly Lys Gln Leu Leu Gly Glu Asn Tyr Arg Asn
            805                 810                 815

Arg Lys Asn Ile Ser Ala Pro His Glu Asp Trp Pro Arg Trp His Met
        820                 825                 830

His Asp Phe Phe His Ser Phe Leu Ile Val Phe Arg Ile Leu Cys Gly
            835                 840                 845

Glu Trp Ile Glu Asn Met Trp Ala Cys Met Glu Val Gly Gln Lys Ser
850                 855                 860

Ile Cys Leu Ile Leu Phe Leu Thr Val Met Val Leu Gly Asn Leu Val
865                 870                 875                 880

Val Leu Asn Leu Phe Ile Ala Leu Leu Leu Asn Ser Phe Ser Ala Asp
            885                 890                 895

Asn Leu Thr Ala Pro Glu Asp Asp Gly Glu Val Asn Asn Leu Gln Val
            900                 905                 910

Ala Leu Ala Arg Ile Gln Val Phe Gly His Arg Thr Lys Gln Ala Leu
            915                 920                 925

Cys Ser Phe Phe Ser Arg Pro Cys Pro Phe Pro Gln Pro Lys Ala Glu
930                 935                 940

Pro Glu Leu Val Val Lys Leu Pro Leu Ser Ser Ser Lys Ala Glu Asn
945                 950                 955                 960

His Val Ala Ala Asn Thr Ala Arg Gly Ser Ser Gly Gly Leu Gln Ala
            965                 970                 975

Pro Arg Gly Pro Arg Asp Glu His Ser Asp Phe Ile Ala Asn Pro Thr
            980                 985                 990

Val Trp Val Ser Val Pro Ile Ala Glu Gly Glu Ser Asp Leu Asp Asp
            995                 1000                1005

Leu Glu Asp Asp Gly Gly Glu Asp Ala Gln Ser Phe Gln Gln Glu
            1010                1015                1020

Val Ile Pro Lys Gly Gln Gln Glu Gln Leu Gln Gln Val Glu Arg
            1025                1030                1035

Cys Gly Asp His Leu Thr Pro Arg Ser Pro Gly Thr Gly Thr Ser
            1040                1045                1050

Ser Glu Asp Leu Ala Pro Ser Leu Gly Glu Thr Trp Lys Asp Glu
            1055                1060                1065

Ser Val Pro Gln Ala Ser Ala Glu Gly Val Asp Asp Thr Ser Ser
            1070                1075                1080

Ser Glu Gly Ser Thr Val Asp Cys Pro Asp Pro Glu Glu Ile Leu
            1085                1090                1095

Arg Lys Ile Pro Glu Leu Ala Asp Asp Leu Glu Glu Pro Asp Asp
            1100                1105                1110

Cys Phe Thr Glu Gly Cys Ile Arg His Cys Pro Cys Cys Lys Val
            1115                1120                1125

Asp Thr Thr Lys Ser Pro Trp Asp Val Gly Trp Gln Val Arg Lys
            1130                1135                1140

Thr Cys Tyr Arg Ile Val Glu His Ser Trp Phe Glu Ser Phe Ile
            1145                1150                1155

Ile Phe Met Ile Leu Leu Ser Ser Gly Ser Leu Ala Phe Glu Asp
            1160                1165                1170

Tyr Tyr Leu Asp Gln Lys Pro Thr Val Lys Ala Leu Leu Glu Tyr
            1175                1180                1185

Thr Asp Arg Val Phe Thr Phe Ile Phe Val Phe Glu Met Leu Leu
            1190                1195                1200

-continued

```
Lys Trp Val Ala Tyr Gly Phe Lys Lys Tyr Phe Thr Asn Ala Trp
    1205                1210                1215
Cys Trp Leu Asp Phe Leu Ile Val Asn Ile Ser Leu Ile Ser Leu
    1220                1225                1230
Thr Ala Lys Ile Leu Glu Tyr Ser Glu Val Ala Pro Ile Lys Ala
    1235                1240                1245
Leu Arg Thr Leu Arg Ala Leu Arg Pro Leu Arg Ala Leu Ser Arg
    1250                1255                1260
Phe Glu Gly Met Arg Val Val Asp Ala Leu Val Gly Ala Ile
    1265                1270                1275
Pro Ser Ile Met Asn Val Leu Leu Val Cys Leu Ile Phe Trp Leu
    1280                1285                1290
Ile Phe Ser Ile Met Gly Val Asn Leu Phe Ala Gly Lys Phe Trp
    1295                1300                1305
Arg Cys Ile Asn Tyr Thr Asp Gly Glu Phe Ser Leu Val Pro Leu
    1310                1315                1320
Ser Ile Val Asn Asn Lys Ser Asp Cys Lys Ile Gln Asn Ser Thr
    1325                1330                1335
Gly Ser Phe Phe Trp Val Asn Val Lys Val Asn Phe Asp Asn Val
    1340                1345                1350
Ala Met Gly Tyr Leu Ala Leu Leu Gln Val Ala Thr Phe Lys Gly
    1355                1360                1365
Trp Met Asp Ile Met Tyr Ala Ala Val Asp Ser Arg Glu Val Asn
    1370                1375                1380
Met Gln Pro Lys Trp Glu Asp Asn Val Tyr Met Tyr Leu Tyr Phe
    1385                1390                1395
Val Ile Phe Ile Ile Phe Gly Gly Phe Phe Thr Leu Asn Leu Phe
    1400                1405                1410
Val Gly Val Ile Ile Asp Asn Phe Asn Gln Gln Lys Lys Lys Leu
    1415                1420                1425
Gly Gly Gln Asp Ile Phe Met Thr Glu Glu Gln Lys Lys Tyr Tyr
    1430                1435                1440
Asn Ala Met Lys Lys Leu Gly Ser Lys Lys Pro Gln Lys Pro Ile
    1445                1450                1455
Pro Arg Pro Leu Asn Lys Phe Gln Gly Phe Val Phe Asp Ile Val
    1460                1465                1470
Thr Arg Gln Ala Phe Asp Ile Thr Ile Met Val Leu Ile Cys Leu
    1475                1480                1485
Asn Met Ile Thr Met Met Val Glu Thr Asp Asp Gln Ser Glu Glu
    1490                1495                1500
Lys Thr Lys Ile Leu Gly Lys Ile Asn Gln Phe Phe Val Ala Val
    1505                1510                1515
Phe Thr Gly Glu Cys Val Met Lys Leu Phe Ala Leu Arg Gln Tyr
    1520                1525                1530
Tyr Phe Thr Asn Gly Trp Asn Val Phe Asp Phe Ile Val Val Val
    1535                1540                1545
Leu Ser Ile Ala Ser Leu Ile Phe Ser Ala Ile Leu Lys Ser Leu
    1550                1555                1560
Gln Ser Tyr Phe Ser Pro Thr Leu Phe Arg Val Ile Arg Leu Ala
    1565                1570                1575
Arg Ile Gly Arg Ile Leu Arg Leu Ile Arg Ala Ala Lys Gly Ile
    1580                1585                1590
Arg Thr Leu Leu Phe Ala Leu Met Met Ser Leu Pro Ala Leu Phe
```

```
                    1595                1600                1605

Asn Ile Gly Leu Leu Leu Phe Leu Val Met Phe Ile Tyr Ser Ile
        1610                1615                1620

Phe Gly Met Ser Ser Phe Pro His Val Arg Trp Glu Ala Gly Ile
    1625                1630                1635

Asp Asp Met Phe Asn Phe Gln Thr Phe Ala Asn Ser Met Leu Cys
    1640                1645                1650

Leu Phe Gln Ile Thr Thr Ser Ala Gly Trp Asp Gly Leu Leu Ser
    1655                1660                1665

Pro Ile Leu Asn Thr Gly Pro Pro Tyr Cys Asp Pro Asn Leu Pro
    1670                1675                1680

Asn Ser Asn Gly Thr Arg Gly Asp Cys Gly Ser Pro Ala Val Gly
    1685                1690                1695

Ile Ile Phe Phe Thr Thr Tyr Ile Ile Ile Ser Phe Leu Ile Val
    1700                1705                1710

Val Asn Met Tyr Ile Ala Val Ile Leu Glu Asn Phe Asn Val Ala
    1715                1720                1725

Thr Glu Glu Ser Thr Glu Pro Leu Ser Glu Asp Asp Phe Asp Met
    1730                1735                1740

Phe Tyr Glu Thr Trp Glu Lys Phe Asp Pro Glu Ala Thr Gln Phe
    1745                1750                1755

Ile Thr Phe Ser Ala Leu Ser Asp Phe Ala Asp Thr Leu Ser Gly
    1760                1765                1770

Pro Leu Arg Ile Pro Lys Pro Asn Arg Asn Ile Leu Ile Gln Met
    1775                1780                1785

Asp Leu Pro Leu Val Pro Gly Asp Lys Ile His Cys Leu Asp Ile
    1790                1795                1800

Leu Phe Ala Phe Thr Lys Asn Val Leu Gly Glu Ser Gly Glu Leu
    1805                1810                1815

Asp Ser Leu Lys Ala Asn Met Glu Glu Lys Phe Met Ala Thr Asn
    1820                1825                1830

Leu Ser Lys Ser Ser Tyr Glu Pro Ile Ala Thr Thr Leu Arg Trp
    1835                1840                1845

Lys Gln Glu Asp Ile Ser Ala Thr Val Ile Gln Lys Ala Tyr Arg
    1850                1855                1860

Ser Tyr Val Leu His Arg Ser Met Ala Leu Ser Asn Thr Pro Cys
    1865                1870                1875

Val Pro Arg Ala Glu Glu Glu Ala Ala Ser Leu Pro Asp Glu Gly
    1880                1885                1890

Phe Val Ala Phe Thr Ala Asn Glu Asn Cys Val Leu Pro Asp Lys
    1895                1900                1905

Ser Glu Thr Ala Ser Ala Thr Ser Phe Pro Pro Ser Tyr Glu Ser
    1910                1915                1920

Val Thr Arg Gly Leu Ser Asp Arg Val Asn Met Arg Thr Ser Ser
    1925                1930                1935

Ser Ile Gln Asn Glu Asp Glu Ala Thr Ser Met Glu Leu Ile Ala
    1940                1945                1950

Pro Gly Pro
    1955

<210> SEQ ID NO 3
<211> LENGTH: 48
<212> TYPE: DNA
<213> ORGANISM: Artificial sequence
<220> FEATURE:
```

```
<223> OTHER INFORMATION: Synthetic primer
<220> FEATURE:
<221> NAME/KEY: misc_feature
<222> LOCATION: (1)..(4)
<223> OTHER INFORMATION: n is a, c, g, or t

<400> SEQUENCE: 3
nnnngttaac ttcgccacca tggaattccc cattggatcc ctcgaaac          48

<210> SEQ ID NO 4
<211> LENGTH: 22
<212> TYPE: DNA
<213> ORGANISM: Artificial sequence
<220> FEATURE:
<223> OTHER INFORMATION: Synthetic primer

<400> SEQUENCE: 4
atggaattcc ccattggatc cc                                     22

<210> SEQ ID NO 5
<211> LENGTH: 19
<212> TYPE: DNA
<213> ORGANISM: Artificial sequence
<220> FEATURE:
<223> OTHER INFORMATION: Synthetic primer

<400> SEQUENCE: 5
cacctgccag cccacatcc                                         19

<210> SEQ ID NO 6
<211> LENGTH: 47
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(4)
<223> OTHER INFORMATION: n is a, c, g, or t

<400> SEQUENCE: 6
nnnngcggcc gcctcactag ggcccagggg caatcagctc catactg           47

<210> SEQ ID NO 7
<211> LENGTH: 24
<212> TYPE: DNA
<213> ORGANISM: Artificial sequence
<220> FEATURE:
<223> OTHER INFORMATION: Synthetic primer

<400> SEQUENCE: 7
ctagggccca ggggcaatca gctc                                   24

<210> SEQ ID NO 8
<211> LENGTH: 21
<212> TYPE: DNA
<213> ORGANISM: Artificial sequence
<220> FEATURE:
<223> OTHER INFORMATION: Synthetic primer

<400> SEQUENCE: 8
gacctggaag aaccagatga c                                      21
```